United States Patent
Fogh et al.

(10) Patent No.: US 12,053,510 B2
(45) Date of Patent: Aug. 6, 2024

(54) TREATMENT OF NEURONAL CEROID LIPOFUSCINOSIS

(71) Applicant: ORFONEURO APS, Lynge (DK)

(72) Inventors: Jens Morten Fogh, Lynge (DK); Paul Saftig, Gettorf (DE); Friederike Zunke, Kiel (DE); André Rosa Alcalde Marques, Kiel (DE)

(73) Assignee: ORFONEURO APS, Lynge (DK)

( * ) Notice: Subject to any disclaimer, the term of this patent is extended or adjusted under 35 U.S.C. 154(b) by 729 days.

(21) Appl. No.: 17/052,445

(22) PCT Filed: May 1, 2019

(86) PCT No.: PCT/EP2019/061140
§ 371 (c)(1),
(2) Date: Nov. 2, 2020

(87) PCT Pub. No.: WO2019/211320
PCT Pub. Date: Nov. 7, 2019

(65) Prior Publication Data
US 2021/0169998 A1    Jun. 10, 2021

(30) Foreign Application Priority Data

May 1, 2018  (EP) .................................... 18170273
Jul. 5, 2018  (EP) .................................... 18182039

(51) Int. Cl.
*A61K 38/48*    (2006.01)
*A61K 9/00*     (2006.01)
(Continued)

(52) U.S. Cl.
CPC .......... *A61K 38/488* (2013.01); *A61K 9/0019* (2013.01); *A61P 25/16* (2018.01); *A61P 25/28* (2018.01)

(58) Field of Classification Search
None
See application file for complete search history.

(56) References Cited

U.S. PATENT DOCUMENTS

| 4,683,202 A | 7/1987 | Mullis |
| 4,879,236 A | 11/1989 | Smith et al. |

(Continued)

FOREIGN PATENT DOCUMENTS

| WO | 2008144591 A2 | 11/2008 |
| WO | 2017075540 A1 | 5/2017 |

OTHER PUBLICATIONS

Shevtsova, Zinayida; et al; "CNS-Expressed Cathepsin D Prevents Lymphopenia in a Murine Model of Congenital Neuronal Ceroid Lipofuscinosis" The American Journal of Pathology 177, 271-279, 2010 (Year: 2010).*

(Continued)

*Primary Examiner* — David W Berke-Schlessel
(74) *Attorney, Agent, or Firm* — Workman Nydegger

(57) ABSTRACT

The invention provides for novel treatments of lysosomal storage diseases, in particular of Neuronal Ceroid Lipofuscinosis (NCL) or synucleinopathy or a disease characterized by block of autophagic flow. The treatment comprises administration of human pro-Cathepsin, in particular human pro-Cathpsin D, B or L to patients in need thereof.

18 Claims, 3 Drawing Sheets

Figure 1:
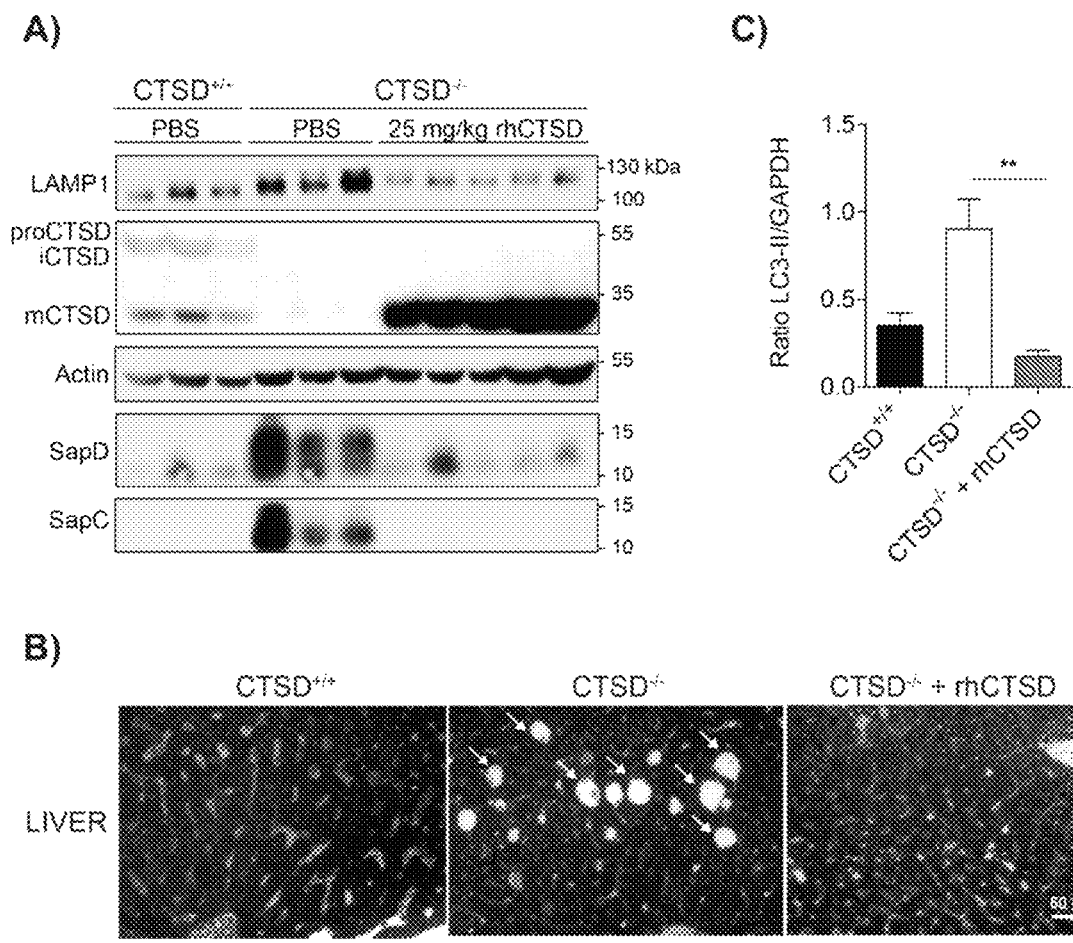

Specification includes a Sequence Listing.

(51) Int. Cl.
  *A61P 25/16* (2006.01)
  *A61P 25/28* (2006.01)

(56) References Cited

U.S. PATENT DOCUMENTS

| | | | |
|---|---|---|---|
| 5,871,986 | A | 2/1999 | Boyce |
| 5,925,565 | A | 7/1999 | Berlioz et al. |
| 5,928,906 | A | 7/1999 | Köster et al. |
| 5,935,819 | A | 8/1999 | Eichner et al. |
| 2011/0064721 | A1 | 3/2011 | Zhang et al. |
| 2014/0044694 | A1 | 2/2014 | Ozono et al. |
| 2017/0333569 | A1 | 11/2017 | Zhang et al. |

OTHER PUBLICATIONS

International Search Report and Written Opinion from PCT Application No. PCT/EP2019/061140, Aug. 6, 2019.
Extended European Search Report from corresponding EP Application No. EP18170273.9, Dec. 11, 2018.
Beyer et al., "Self-activation of Recombinant Human Lysosomal Procathepsin D at a Newly Engineered Cleavage Junction, "Short" Pseudocathepsin D", The Journal of Biological Chemistry, vol. 271, No. 26, Jun. 28, 1996, pp. 15590-15596.
Blanz et al., "Reversal of Peripheral and Central Neural Storage and Ataxia After Recombinant Enzyme Replacement Therapy in α-mannosidosis Mice", Human Molecular Genetics, vol. 17, No. 22, Aug. 19, 2008, pp. 3437-3445.
Di Domenico et al., "Cathepsin D as a Therapeutic Target in Alzheimer's Disease", Expert Opinion on Therapeutic Targets, vol. 20, No. 12, Nov. 2, 2016, pp. 1393-1395.
Kohan et al., "Therapeutic Approaches to the Challenge of Neuronal Ceroid Lipofuscinoses", Curr Pharm Biotechnol, vol. 12, No. 6, Jun. 1, 2011, pp. 867-883.
Mazzulli et al., "Gaucher's Disease Glucocerebrosidase and <alpha>-synuclein Form a Bidirectional Pathogenic Loop in Synucleinopathies", Cell, vol. 146, No. 1, Jul. 8, 2011, pp. 37-52.
Meng et al., "Effective Intravenous Therapy for Neurodegenerative Disease With a Therapeutic Enzyme and a Peptide That Mediates Delivery to the Brain", Molecular Therapy, vol. 22, No. 3, Mar. 31, 2014, pp. 547-553.
Meng et al., "A Basic ApoE-Based Peptide Mediator to Deliver Proteins Across the Blood-Brain Barrier: Long-Term Efficacy, Toxicity, and Mechanism", Molecular Therapy, vol. 25, No. 7, Jul. 31, 2017, pp. 1531-1543.
Neverman et al., "Experimental Therapies in the Neuronal Ceroid Lipofuscinoses", Biochimica et Biophysica Acta, vol. 1852, No. 10, May 6, 2015, pp. 2292-2300.
Saftig et al., "Mice Deficient for the Lysosomal Proteinase Cathepsin D Exhibit Progressive Atrophy of the Intestinal Mucosa and Profound Destruction of Lymphoid Cells", The EMBO Journal, vol. 14, No. 15, Mar. 24, 1995, pp. 3599-3608.
Sarkar et al., "Peptide Carrier-Mediated Non-Covalent Delivery of Unmodified Cisplatin, Methotrexate and Other Agents via Intravenous Route to the Brain", PLOS One, vol. 9, No. 5, May 21, 2014, 10 pages.
Siintola et al., "Cathepsin D Deficiency Underlies Congenital Human Neuronal Ceroid-lipofuscinosis", Brain, vol. 129, No. 6, May 2, 2006, pp. 1438-1445.
Vidoni et al., "The Role of Cathepsin D in the Pathogenesis of Human Neurodegenerative Disorders", Medicinal Research Reviews, vol. 36, No. 5, Sep. 1, 2016, pp. 845-870.

* cited by examiner

SEQUENCE LISTING

<160> NUMBER OF SEQ ID NOS: 17

<210> SEQ ID NO 1
<211> LENGTH: 1239
<212> TYPE: DNA
<213> ORGANISM: Hiomo sapiens
<220> FEATURE:
<221> NAME/KEY: CDS
<222> LOCATION: (1)..(1239)
<220> FEATURE:
<221> NAME/KEY: sig_peptide
<222> LOCATION: (1)..(60)

<400> SEQUENCE: 1

```
atg cag ccc tcc agc ctt ctg ccg ctc gcc ctc tgc ctg ctg gct gca      48
Met Gln Pro Ser Ser Leu Leu Pro Leu Ala Leu Cys Leu Leu Ala Ala
1               5                   10                  15 ccc gcc tcc gcg ctc gtc agg atc ccg ctg cac aag ttc acg tcc atc      96
Pro Ala Ser Ala Leu Val Arg Ile Pro Leu His Lys Phe Thr Ser Ile
                20                  25                  30 cgc cgg acc atg tcg gag gtt ggg ggc tct gtg gag gac ctg att gcc     144
Arg Arg Thr Met Ser Glu Val Gly Gly Ser Val Glu Asp Leu Ile Ala
            35                  40                  45 aaa ggc ccc gtc tca aag tac tcc cag gcg gtg cca gcc gtg acc gag     192
Lys Gly Pro Val Ser Lys Tyr Ser Gln Ala Val Pro Ala Val Thr Glu
        50                  55                  60 ggg ccc att ccc gag gtg ctc aag aac tac atg gac gcc cag tac tac     240
Gly Pro Ile Pro Glu Val Leu Lys Asn Tyr Met Asp Ala Gln Tyr Tyr
65                  70                  75                  80 ggg gag att ggc atc ggg acg ccc ccc cag tgc ttc aca gtc gtc ttc     288
Gly Glu Ile Gly Ile Gly Thr Pro Pro Gln Cys Phe Thr Val Val Phe
                85                  90                  95 gac acg ggc tcc tcc aac ctg tgg gtc ccc tcc atc cac tgc aaa ctg     336
Asp Thr Gly Ser Ser Asn Leu Trp Val Pro Ser Ile His Cys Lys Leu
                100                 105                 110 ctg gac atc gct tgc tgg atc cac cac aag tac aac agc gac aag tcc     384
Leu Asp Ile Ala Cys Trp Ile His His Lys Tyr Asn Ser Asp Lys Ser
            115                 120                 125 agc acc tac gtg aag aat ggt acc tcg ttt gac atc cac tat ggc tcg     432
Ser Thr Tyr Val Lys Asn Gly Thr Ser Phe Asp Ile His Tyr Gly Ser
        130                 135                 140 ggc agc ctc tcc ggg tac ctg agc cag gac act gtg tcg gtg ccc tgc     480
Gly Ser Leu Ser Gly Tyr Leu Ser Gln Asp Thr Val Ser Val Pro Cys
145                 150                 155                 160 cag tca gcg tcg tca gcc tct gcc ctg ggc ggt gtc aaa gtg gag agg     528
Gln Ser Ala Ser Ser Ala Ser Ala Leu Gly Gly Val Lys Val Glu Arg
                165                 170                 175 cag gtc ttt ggg gag gcc acc aag cag cca ggc atc acc ttc atc gca     576
Gln Val Phe Gly Glu Ala Thr Lys Gln Pro Gly Ile Thr Phe Ile Ala
                180                 185                 190 gcc aag ttc gat ggc atc ctg ggc atg gcc tac ccc cgc atc tcc gtc     624
Ala Lys Phe Asp Gly Ile Leu Gly Met Ala Tyr Pro Arg Ile Ser Val
            195                 200                 205 aac aac gtg ctg ccc gtc ttc gac aac ctg atg cag cag aag ctg gtg     672
Asn Asn Val Leu Pro Val Phe Asp Asn Leu Met Gln Gln Lys Leu Val
        210                 215                 220 gac cag aac atc ttc tcc ttc tac ctg agc agg gac cca gat gcg cag     720
Asp Gln Asn Ile Phe Ser Phe Tyr Leu Ser Arg Asp Pro Asp Ala Gln
225                 230                 235                 240 cct ggg ggt gag ctg atg ctg ggt ggc aca gac tcc aag tat tac aag     768
Pro Gly Gly Glu Leu Met Leu Gly Gly Thr Asp Ser Lys Tyr Tyr Lys
                245                 250                 255
```

-continued

```
ggt tct ctg tcc tac ctg aat gtc acc cgc aag gcc tac tgg cag gtc      816
Gly Ser Leu Ser Tyr Leu Asn Val Thr Arg Lys Ala Tyr Trp Gln Val
        260                 265                 270 cac ctg gac cag gtg gag gtg gcc agc ggg ctg acc ctg tgc aag gag      864
His Leu Asp Gln Val Glu Val Ala Ser Gly Leu Thr Leu Cys Lys Glu
    275                 280                 285 ggc tgt gag gcc att gtg gac aca ggc act tcc ctc atg gtg ggc ccg      912
Gly Cys Glu Ala Ile Val Asp Thr Gly Thr Ser Leu Met Val Gly Pro
290                 295                 300 gtg gat gag gtg cgc gag ctg cag aag gcc atc ggg gcc gtg ccg ctg      960
Val Asp Glu Val Arg Glu Leu Gln Lys Ala Ile Gly Ala Val Pro Leu
305                 310                 315                 320 att cag ggc gag tac atg atc ccc tgt gag aag gtg tcc acc ctg ccc      1008
Ile Gln Gly Glu Tyr Met Ile Pro Cys Glu Lys Val Ser Thr Leu Pro
            325                 330                 335 gcg atc aca ctg aag ctg gga ggc aaa ggc tac aag ctg tcc cca gag      1056
Ala Ile Thr Leu Lys Leu Gly Gly Lys Gly Tyr Lys Leu Ser Pro Glu
        340                 345                 350 gac tac acg ctc aag gtg tcg cag gcc ggg aag acc ctc tgc ctg agc      1104
Asp Tyr Thr Leu Lys Val Ser Gln Ala Gly Lys Thr Leu Cys Leu Ser
    355                 360                 365 ggc ttc atg ggc atg gac atc ccg cca ccc agc ggg cca ctc tgg atc      1152
Gly Phe Met Gly Met Asp Ile Pro Pro Pro Ser Gly Pro Leu Trp Ile
370                 375                 380 ctg ggc gac gtc ttc atc ggc cgc tac tac act gtg ttt gac cgt gac      1200
Leu Gly Asp Val Phe Ile Gly Arg Tyr Tyr Thr Val Phe Asp Arg Asp
385                 390                 395                 400 aac aac agg gtg ggc ttc gcc gag gct gcc cgc ctc tag              1239
Asn Asn Arg Val Gly Phe Ala Glu Ala Ala Arg Leu
            405                 410
```

<210> SEQ ID NO 2
<211> LENGTH: 412
<212> TYPE: PRT
<213> ORGANISM: Hiomo sapiens

<400> SEQUENCE: 2

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
        35                  40                  45

Lys Gly Pro Val Ser Lys Tyr Ser Gln Ala Val Pro Ala Val Thr Glu
    50                  55                  60

Gly Pro Ile Pro Glu Val Leu Lys Asn Tyr Met Asp Ala Gln Tyr Tyr
65                  70                  75                  80

Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160
```

```
Gln Ser Ala Ser Ser Ala Ser Ala Leu Gly Gly Val Lys Val Glu Arg
            165                 170                 175

Gln Val Phe Gly Glu Ala Thr Lys Gln Pro Gly Ile Thr Phe Ile Ala
        180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
                260                 265                 270

His Leu Asp Gln Val Glu Val Ala Ser Gly Leu Thr Leu Cys Lys Glu
            275                 280                 285

Gly Cys Glu Ala Ile Val Asp Thr Gly Thr Ser Leu Met Val Gly Pro
        290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu
                340                 345                 350

Asp Tyr Thr Leu Lys Val Ser Gln Ala Gly Lys Thr Leu Cys Leu Ser
            355                 360                 365

Gly Phe Met Gly Met Asp Ile Pro Pro Pro Ser Gly Pro Leu Trp Ile
        370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410

<210> SEQ ID NO 3
<211> LENGTH: 392
<212> TYPE: PRT
<213> ORGANISM: Homo sapiens
<220> FEATURE:
<221> NAME/KEY: MISC_FEATURE
<222> LOCATION: (1)..(392)
<223> OTHER INFORMATION: SEQ ID NO: 2, residues 21-412

<400> SEQUENCE: 3

Leu Val Arg Ile Pro Leu His Lys Phe Thr Ser Ile Arg Arg Thr Met
1               5                   10                  15

Ser Glu Val Gly Gly Ser Val Glu Asp Leu Ile Ala Lys Gly Pro Val
            20                  25                  30

Ser Lys Tyr Ser Gln Ala Val Pro Ala Val Thr Glu Gly Pro Ile Pro
        35                  40                  45

Glu Val Leu Lys Asn Tyr Met Asp Ala Gln Tyr Tyr Gly Glu Ile Gly
    50                  55                  60

Ile Gly Thr Pro Pro Gln Cys Phe Thr Val Val Phe Asp Thr Gly Ser
65                  70                  75                  80

Ser Asn Leu Trp Val Pro Ser Ile His Cys Lys Leu Leu Asp Ile Ala
                85                  90                  95

Cys Trp Ile His His Lys Tyr Asn Ser Asp Lys Ser Ser Thr Tyr Val
```

```
                100                 105                 110
Lys Asn Gly Thr Ser Phe Asp Ile His Tyr Gly Ser Gly Ser Leu Ser
            115                 120                 125

Gly Tyr Leu Ser Gln Asp Thr Val Ser Val Pro Cys Gln Ser Ala Ser
        130                 135                 140

Ser Ala Ser Ala Leu Gly Gly Val Lys Val Glu Arg Gln Val Phe Gly
145                 150                 155                 160

Glu Ala Thr Lys Gln Pro Gly Ile Thr Phe Ile Ala Ala Lys Phe Asp
                165                 170                 175

Gly Ile Leu Gly Met Ala Tyr Pro Arg Ile Ser Val Asn Asn Val Leu
            180                 185                 190

Pro Val Phe Asp Asn Leu Met Gln Gln Lys Leu Val Asp Gln Asn Ile
        195                 200                 205

Phe Ser Phe Tyr Leu Ser Arg Asp Pro Asp Ala Gln Pro Gly Gly Glu
    210                 215                 220

Leu Met Leu Gly Gly Thr Asp Ser Lys Tyr Tyr Lys Gly Ser Leu Ser
225                 230                 235                 240

Tyr Leu Asn Val Thr Arg Lys Ala Tyr Trp Gln Val His Leu Asp Gln
                245                 250                 255

Val Glu Val Ala Ser Gly Leu Thr Leu Cys Lys Glu Gly Cys Glu Ala
            260                 265                 270

Ile Val Asp Thr Gly Thr Ser Leu Met Val Gly Pro Val Asp Glu Val
        275                 280                 285

Arg Glu Leu Gln Lys Ala Ile Gly Ala Val Pro Leu Ile Gln Gly Glu
    290                 295                 300

Tyr Met Ile Pro Cys Glu Lys Val Ser Thr Leu Pro Ala Ile Thr Leu
305                 310                 315                 320

Lys Leu Gly Gly Lys Gly Tyr Lys Leu Ser Pro Glu Asp Tyr Thr Leu
                325                 330                 335

Lys Val Ser Gln Ala Gly Lys Thr Leu Cys Leu Ser Gly Phe Met Gly
            340                 345                 350

Met Asp Ile Pro Pro Pro Ser Gly Pro Leu Trp Ile Leu Gly Asp Val
        355                 360                 365

Phe Ile Gly Arg Tyr Tyr Thr Val Phe Asp Arg Asp Asn Asn Arg Val
    370                 375                 380

Gly Phe Ala Glu Ala Ala Arg Leu
385                 390

<210> SEQ ID NO 4
<211> LENGTH: 348
<212> TYPE: PRT
<213> ORGANISM: Homo sapiens
<220> FEATURE:
<221> NAME/KEY: MISC_FEATURE
<222> LOCATION: (1)..(348)
<223> OTHER INFORMATION: SEQ ID NO: 2, residues 65-412

<400> SEQUENCE: 4

Gly Pro Ile Pro Glu Val Leu Lys Asn Tyr Met Asp Ala Gln Tyr Tyr
1               5                   10                  15

Gly Glu Ile Gly Ile Gly Thr Pro Pro Gln Cys Phe Thr Val Val Phe
            20                  25                  30

Asp Thr Gly Ser Ser Asn Leu Trp Val Pro Ser Ile His Cys Lys Leu
        35                  40                  45

Leu Asp Ile Ala Cys Trp Ile His His Lys Tyr Asn Ser Asp Lys Ser
    50                  55                  60
```

-continued

```
Ser Thr Tyr Val Lys Asn Gly Thr Ser Phe Asp Ile His Tyr Gly Ser
 65                  70                  75                  80

Gly Ser Leu Ser Gly Tyr Leu Ser Gln Asp Thr Val Ser Val Pro Cys
                 85                  90                  95

Gln Ser Ala Ser Ala Ser Ala Leu Gly Gly Val Lys Val Glu Arg
            100                 105                 110

Gln Val Phe Gly Glu Ala Thr Lys Gln Pro Gly Ile Thr Phe Ile Ala
            115                 120                 125

Ala Lys Phe Asp Gly Ile Leu Gly Met Ala Tyr Pro Arg Ile Ser Val
            130                 135                 140

Asn Asn Val Leu Pro Val Phe Asp Asn Leu Met Gln Gln Lys Leu Val
145                 150                 155                 160

Asp Gln Asn Ile Phe Ser Phe Tyr Leu Ser Arg Asp Pro Asp Ala Gln
                165                 170                 175

Pro Gly Gly Glu Leu Met Leu Gly Gly Thr Asp Ser Lys Tyr Tyr Lys
            180                 185                 190

Gly Ser Leu Ser Tyr Leu Asn Val Thr Arg Lys Ala Tyr Trp Gln Val
            195                 200                 205

His Leu Asp Gln Val Glu Val Ala Ser Gly Leu Thr Leu Cys Lys Glu
    210                 215                 220

Gly Cys Glu Ala Ile Val Asp Thr Gly Thr Ser Leu Met Val Gly Pro
225                 230                 235                 240

Val Asp Glu Val Arg Glu Leu Gln Lys Ala Ile Gly Ala Val Pro Leu
                245                 250                 255

Ile Gln Gly Glu Tyr Met Ile Pro Cys Glu Lys Val Ser Thr Leu Pro
            260                 265                 270

Ala Ile Thr Leu Lys Leu Gly Gly Lys Gly Tyr Lys Leu Ser Pro Glu
            275                 280                 285

Asp Tyr Thr Leu Lys Val Ser Gln Ala Gly Lys Thr Leu Cys Leu Ser
            290                 295                 300

Gly Phe Met Gly Met Asp Ile Pro Pro Pro Ser Gly Pro Leu Trp Ile
305                 310                 315                 320

Leu Gly Asp Val Phe Ile Gly Arg Tyr Tyr Thr Val Phe Asp Arg Asp
                325                 330                 335

Asn Asn Arg Val Gly Phe Ala Glu Ala Ala Arg Leu
            340                 345
```

<210> SEQ ID NO 5
<211> LENGTH: 98
<212> TYPE: PRT
<213> ORGANISM: Homo sapiens
<220> FEATURE:
<221> NAME/KEY: MISC_FEATURE
<222> LOCATION: (1)..(98)
<223> OTHER INFORMATION: SEQ ID NO: 2, residues 65-162

<400> SEQUENCE: 5

```
Gly Pro Ile Pro Glu Val Leu Lys Asn Tyr Met Asp Ala Gln Tyr Tyr
 1               5                  10                  15

Gly Glu Ile Gly Ile Gly Thr Pro Pro Gln Cys Phe Thr Val Val Phe
                20                  25                  30

Asp Thr Gly Ser Ser Asn Leu Trp Val Pro Ser Ile His Cys Lys Leu
            35                  40                  45

Leu Asp Ile Ala Cys Trp Ile His His Lys Tyr Asn Ser Asp Lys Ser
     50                  55                  60
```

```
Ser Thr Tyr Val Lys Asn Gly Thr Ser Phe Asp Ile His Tyr Gly Ser
 65                  70                  75                  80

Gly Ser Leu Ser Gly Tyr Leu Ser Gln Asp Thr Val Ser Val Pro Cys
                 85                  90                  95

Gln Ser
```

```
<210> SEQ ID NO 6
<211> LENGTH: 244
<212> TYPE: PRT
<213> ORGANISM: Homo sapiens
<220> FEATURE:
<221> NAME/KEY: MISC_FEATURE
<222> LOCATION: (1)..(244)
<223> OTHER INFORMATION: SEQ ID NO: 2, residues 169-412

<400> SEQUENCE: 6

Leu Gly Gly Val Lys Val Glu Arg Gln Val Phe Gly Glu Ala Thr Lys
 1               5                  10                  15

Gln Pro Gly Ile Thr Phe Ile Ala Ala Lys Phe Asp Gly Ile Leu Gly
                 20                  25                  30

Met Ala Tyr Pro Arg Ile Ser Val Asn Asn Val Leu Pro Val Phe Asp
                 35                  40                  45

Asn Leu Met Gln Gln Lys Leu Val Asp Gln Asn Ile Phe Ser Phe Tyr
 50                  55                  60

Leu Ser Arg Asp Pro Asp Ala Gln Pro Gly Gly Glu Leu Met Leu Gly
 65                  70                  75                  80

Gly Thr Asp Ser Lys Tyr Tyr Lys Gly Ser Leu Ser Tyr Leu Asn Val
                 85                  90                  95

Thr Arg Lys Ala Tyr Trp Gln Val His Leu Asp Gln Val Glu Val Ala
                100                 105                 110

Ser Gly Leu Thr Leu Cys Lys Glu Gly Cys Glu Ala Ile Val Asp Thr
                115                 120                 125

Gly Thr Ser Leu Met Val Gly Pro Val Asp Glu Val Arg Glu Leu Gln
                130                 135                 140

Lys Ala Ile Gly Ala Val Pro Leu Ile Gln Gly Glu Tyr Met Ile Pro
145                 150                 155                 160

Cys Glu Lys Val Ser Thr Leu Pro Ala Ile Thr Leu Lys Leu Gly Gly
                165                 170                 175

Lys Gly Tyr Lys Leu Ser Pro Glu Asp Tyr Thr Leu Lys Val Ser Gln
                180                 185                 190

Ala Gly Lys Thr Leu Cys Leu Ser Gly Phe Met Gly Met Asp Ile Pro
                195                 200                 205

Pro Pro Ser Gly Pro Leu Trp Ile Leu Gly Asp Val Phe Ile Gly Arg
                210                 215                 220

Tyr Tyr Thr Val Phe Asp Arg Asp Asn Asn Arg Val Gly Phe Ala Glu
225                 230                 235                 240

Ala Ala Arg Leu
```

```
<210> SEQ ID NO 7
<211> LENGTH: 1020
<212> TYPE: DNA
<213> ORGANISM: Homo Sapiens
<220> FEATURE:
<221> NAME/KEY: CDS
<222> LOCATION: (1)..(1020)

<400> SEQUENCE: 7 atg tgg cag ctc tgg gcc tcc ctc tgc tgc ctg ctg gtg ttg gcc aat    48
```

```
Met Trp Gln Leu Trp Ala Ser Leu Cys Cys Leu Leu Val Leu Ala Asn
1               5                   10                  15 gcc cgg agc agg ccc tct ttc cat ccc ctg tcg gat gag ctg gtc aac      96
Ala Arg Ser Arg Pro Ser Phe His Pro Leu Ser Asp Glu Leu Val Asn
            20                  25                  30 tat gtc aac aaa cgg aat acc acg tgg cag gcc ggg cac aac ttc tac     144
Tyr Val Asn Lys Arg Asn Thr Thr Trp Gln Ala Gly His Asn Phe Tyr
                35                  40                  45 aac gtg gac atg agc tac ttg aag agg cta tgt ggt acc ttc ctg ggt     192
Asn Val Asp Met Ser Tyr Leu Lys Arg Leu Cys Gly Thr Phe Leu Gly
        50                  55                  60 ggg ccc aag cca ccc cag aga gtt atg ttt acc gag gac ctg aag ctg     240
Gly Pro Lys Pro Pro Gln Arg Val Met Phe Thr Glu Asp Leu Lys Leu
65                  70                  75                  80 cct gca agc ttc gat gca cgg gaa caa tgg cca cag tgt ccc acc atc     288
Pro Ala Ser Phe Asp Ala Arg Glu Gln Trp Pro Gln Cys Pro Thr Ile
                85                  90                  95 aaa gag atc aga gac cag ggc tcc tgt ggc tcc tgc tgg gcc ttc ggg     336
Lys Glu Ile Arg Asp Gln Gly Ser Cys Gly Ser Cys Trp Ala Phe Gly
                100                 105                 110 gct gtg gaa gcc atc tct gac cgg atc tgc atc cac acc aat gcg cac     384
Ala Val Glu Ala Ile Ser Asp Arg Ile Cys Ile His Thr Asn Ala His
            115                 120                 125 gtc agc gtg gag gtg tcg gcg gag gac ctg ctc aca tgc tgt ggc agc     432
Val Ser Val Glu Val Ser Ala Glu Asp Leu Leu Thr Cys Cys Gly Ser
130                 135                 140 atg tgt ggg gac ggc tgt aat ggt ggc tat cct gct gaa gct tgg aac     480
Met Cys Gly Asp Gly Cys Asn Gly Gly Tyr Pro Ala Glu Ala Trp Asn
145                 150                 155                 160 ttc tgg aca aga aaa ggc ctg gtt tct ggt ggc ctc tat gaa tcc cat     528
Phe Trp Thr Arg Lys Gly Leu Val Ser Gly Gly Leu Tyr Glu Ser His
                165                 170                 175 gta ggg tgc aga ccg tac tcc atc cct ccc tgt gag cac cac gtc aac     576
Val Gly Cys Arg Pro Tyr Ser Ile Pro Pro Cys Glu His His Val Asn
            180                 185                 190 ggc tcc cgg ccc cca tgc acg ggg gag gga gat acc ccc aag tgt agc     624
Gly Ser Arg Pro Pro Cys Thr Gly Glu Gly Asp Thr Pro Lys Cys Ser
        195                 200                 205 aag atc tgt gag cct ggc tac agc ccg acc tac aaa cag gac aag cac     672
Lys Ile Cys Glu Pro Gly Tyr Ser Pro Thr Tyr Lys Gln Asp Lys His
210                 215                 220 tac gga tac aat tcc tac agc gtc tcc aat agc gag aag gac atc atg     720
Tyr Gly Tyr Asn Ser Tyr Ser Val Ser Asn Ser Glu Lys Asp Ile Met
225                 230                 235                 240 gcc gag atc tac aaa aac ggc ccc gtg gag gga gct ttc tct gtg tat     768
Ala Glu Ile Tyr Lys Asn Gly Pro Val Glu Gly Ala Phe Ser Val Tyr
                245                 250                 255 tcg gac ttc ctg ctc tac aag tca gga gtg tac caa cac gtc acc gga     816
Ser Asp Phe Leu Leu Tyr Lys Ser Gly Val Tyr Gln His Val Thr Gly
            260                 265                 270 gag atg atg ggt ggc cat gcc atc cgc atc ctg ggc tgg gga gtg gag     864
Glu Met Met Gly Gly His Ala Ile Arg Ile Leu Gly Trp Gly Val Glu
        275                 280                 285 aat ggc aca ccc tac tgg ctg gtt gcc aac tcc tgg aac act gac tgg     912
Asn Gly Thr Pro Tyr Trp Leu Val Ala Asn Ser Trp Asn Thr Asp Trp
    290                 295                 300 ggt gac aat ggc ttc ttt aaa ata ctc aga gga cag gat cac tgt gga     960
Gly Asp Asn Gly Phe Phe Lys Ile Leu Arg Gly Gln Asp His Cys Gly
305                 310                 315                 320
```

```
atc gaa tca gaa gtg gtg gct gga att cca cgc acc gat cag tac tgg    1008
Ile Glu Ser Glu Val Val Ala Gly Ile Pro Arg Thr Asp Gln Tyr Trp
            325                 330                 335 gaa aag atc taa                                                    1020
Glu Lys Ile
```

```
<210> SEQ ID NO 8
<211> LENGTH: 339
<212> TYPE: PRT
<213> ORGANISM: Homo Sapiens

<400> SEQUENCE: 8
```

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 9
<211> LENGTH: 322
<212> TYPE: PRT
<213> ORGANISM: Homo sapiens

<400> SEQUENCE: 9

Arg Ser Arg Pro Ser Phe His Pro Leu Ser Asp Glu Leu Val Asn Tyr
1               5                   10                  15

Val Asn Lys Arg Asn Thr Thr Trp Gln Ala Gly His Asn Phe Tyr Asn
            20                  25                  30

Val Asp Met Ser Tyr Leu Lys Arg Leu Cys Gly Thr Phe Leu Gly Gly
        35                  40                  45

Pro Lys Pro Pro Gln Arg Val Met Phe Thr Glu Asp Leu Lys Leu Pro
    50                  55                  60

Ala Ser Phe Asp Ala Arg Glu Gln Trp Pro Gln Cys Pro Thr Ile Lys
65                  70                  75                  80

Glu Ile Arg Asp Gln Gly Ser Cys Gly Ser Cys Trp Ala Phe Gly Ala
                85                  90                  95

Val Glu Ala Ile Ser Asp Arg Ile Cys Ile His Thr Asn Ala His Val
            100                 105                 110

Ser Val Glu Val Ser Ala Glu Asp Leu Leu Thr Cys Cys Gly Ser Met
        115                 120                 125

Cys Gly Asp Gly Cys Asn Gly Gly Tyr Pro Ala Glu Ala Trp Asn Phe
    130                 135                 140

Trp Thr Arg Lys Gly Leu Val Ser Gly Gly Leu Tyr Glu Ser His Val
145                 150                 155                 160

Gly Cys Arg Pro Tyr Ser Ile Pro Pro Cys Glu His His Val Asn Gly
                165                 170                 175

Ser Arg Pro Pro Cys Thr Gly Glu Gly Asp Thr Pro Lys Cys Ser Lys
            180                 185                 190

Ile Cys Glu Pro Gly Tyr Ser Pro Thr Tyr Lys Gln Asp Lys His Tyr
        195                 200                 205

Gly Tyr Asn Ser Tyr Ser Val Ser Asn Ser Glu Lys Asp Ile Met Ala
    210                 215                 220

Glu Ile Tyr Lys Asn Gly Pro Val Glu Gly Ala Phe Ser Val Tyr Ser
225                 230                 235                 240

Asp Phe Leu Leu Tyr Lys Ser Gly Val Tyr Gln His Val Thr Gly Glu
                245                 250                 255

Met Met Gly Gly His Ala Ile Arg Ile Leu Gly Trp Gly Val Glu Asn
            260                 265                 270

Gly Thr Pro Tyr Trp Leu Val Ala Asn Ser Trp Asn Thr Asp Trp Gly
        275                 280                 285

Asp Asn Gly Phe Phe Lys Ile Leu Arg Gly Gln Asp His Cys Gly Ile
    290                 295                 300

Glu Ser Glu Val Val Ala Gly Ile Pro Arg Thr Asp Gln Tyr Trp Glu
305                 310                 315                 320

Lys Ile

<210> SEQ ID NO 10
<211> LENGTH: 254
<212> TYPE: PRT
<213> ORGANISM: Homo sapiens

<400> SEQUENCE: 10

```
Leu Pro Ala Ser Phe Asp Ala Arg Glu Gln Trp Pro Gln Cys Pro Thr
1               5                   10                  15

Ile Lys Glu Ile Arg Asp Gln Gly Ser Cys Gly Ser Cys Trp Ala Phe
            20                  25                  30

Gly Ala Val Glu Ala Ile Ser Asp Arg Ile Cys Ile His Thr Asn Ala
        35                  40                  45

His Val Ser Val Glu Val Ser Ala Glu Asp Leu Leu Thr Cys Cys Gly
    50                  55                  60

Ser Met Cys Gly Asp Gly Cys Asn Gly Gly Tyr Pro Ala Glu Ala Trp
65                  70                  75                  80

Asn Phe Trp Thr Arg Lys Gly Leu Val Ser Gly Gly Leu Tyr Glu Ser
                85                  90                  95

His Val Gly Cys Arg Pro Tyr Ser Ile Pro Pro Cys Glu His His Val
            100                 105                 110

Asn Gly Ser Arg Pro Pro Cys Thr Gly Glu Gly Asp Thr Pro Lys Cys
        115                 120                 125

Ser Lys Ile Cys Glu Pro Gly Tyr Ser Pro Thr Tyr Lys Gln Asp Lys
    130                 135                 140

His Tyr Gly Tyr Asn Ser Tyr Ser Val Ser Asn Ser Glu Lys Asp Ile
145                 150                 155                 160

Met Ala Glu Ile Tyr Lys Asn Gly Pro Val Glu Gly Ala Phe Ser Val
                165                 170                 175

Tyr Ser Asp Phe Leu Leu Tyr Lys Ser Gly Val Tyr Gln His Val Thr
            180                 185                 190

Gly Glu Met Met Gly Gly His Ala Ile Arg Ile Leu Gly Trp Gly Val
        195                 200                 205

Glu Asn Gly Thr Pro Tyr Trp Leu Val Ala Asn Ser Trp Asn Thr Asp
    210                 215                 220

Trp Gly Asp Asn Gly Phe Phe Lys Ile Leu Arg Gly Gln Asp His Cys
225                 230                 235                 240

Gly Ile Glu Ser Glu Val Val Ala Gly Ile Pro Arg Thr Asp
                245                 250

<210> SEQ ID NO 11
<211> LENGTH: 47
<212> TYPE: PRT
<213> ORGANISM: Homo sapiens

<400> SEQUENCE: 11

Leu Pro Ala Ser Phe Asp Ala Arg Glu Gln Trp Pro Gln Cys Pro Thr
1               5                   10                  15

Ile Lys Glu Ile Arg Asp Gln Gly Ser Cys Gly Ser Cys Trp Ala Phe
            20                  25                  30

Gly Ala Val Glu Ala Ile Ser Asp Arg Ile Cys Ile His Thr Asn
        35                  40                  45

<210> SEQ ID NO 12
<211> LENGTH: 205
<212> TYPE: PRT
<213> ORGANISM: Homo sapiens

<400> SEQUENCE: 12

Val Ser Val Glu Val Ser Ala Glu Asp Leu Leu Thr Cys Cys Gly Ser
1               5                   10                  15

Met Cys Gly Asp Gly Cys Asn Gly Gly Tyr Pro Ala Glu Ala Trp Asn
            20                  25                  30
```

Phe Trp Thr Arg Lys Gly Leu Val Ser Gly Gly Leu Tyr Glu Ser His
            35                  40                  45

Val Gly Cys Arg Pro Tyr Ser Ile Pro Pro Cys Glu His His Val Asn
 50                  55                  60

Gly Ser Arg Pro Pro Cys Thr Gly Glu Gly Asp Thr Pro Lys Cys Ser
 65                  70                  75                  80

Lys Ile Cys Glu Pro Gly Tyr Ser Pro Thr Tyr Lys Gln Asp Lys His
                 85                  90                  95

Tyr Gly Tyr Asn Ser Tyr Ser Val Ser Asn Ser Glu Lys Asp Ile Met
            100                 105                 110

Ala Glu Ile Tyr Lys Asn Gly Pro Val Glu Gly Ala Phe Ser Val Tyr
        115                 120                 125

Ser Asp Phe Leu Leu Tyr Lys Ser Gly Val Tyr Gln His Val Thr Gly
    130                 135                 140

Glu Met Met Gly Gly His Ala Ile Arg Ile Leu Gly Trp Gly Val Glu
145                 150                 155                 160

Asn Gly Thr Pro Tyr Trp Leu Val Ala Asn Ser Trp Asn Thr Asp Trp
                165                 170                 175

Gly Asp Asn Gly Phe Phe Lys Ile Leu Arg Gly Gln Asp His Cys Gly
            180                 185                 190

Ile Glu Ser Glu Val Val Ala Gly Ile Pro Arg Thr Asp
        195                 200                 205

<210> SEQ ID NO 13
<211> LENGTH: 333
<212> TYPE: PRT
<213> ORGANISM: Homo sapiens

<400> SEQUENCE: 13

Met Asn Pro Thr Leu Ile Leu Ala Ala Phe Cys Leu Gly Ile Ala Ser
  1               5                  10                  15

Ala Thr Leu Thr Phe Asp His Ser Leu Glu Ala Gln Trp Thr Lys Trp
             20                  25                  30

Lys Ala Met His Asn Arg Leu Tyr Gly Met Asn Glu Glu Gly Trp Arg
         35                  40                  45

Arg Ala Val Trp Glu Lys Asn Met Lys Met Ile Glu Leu His Asn Gln
 50                  55                  60

Glu Tyr Arg Glu Gly Lys His Ser Phe Thr Met Ala Met Asn Ala Phe
 65                  70                  75                  80

Gly Asp Met Thr Ser Glu Glu Phe Arg Gln Val Met Asn Gly Phe Gln
                 85                  90                  95

Asn Arg Lys Pro Arg Lys Gly Lys Val Phe Gln Glu Pro Leu Phe Tyr
            100                 105                 110

Glu Ala Pro Arg Ser Val Asp Trp Arg Glu Lys Gly Tyr Val Thr Pro
        115                 120                 125

Val Lys Asn Gln Gly Gln Cys Gly Ser Cys Trp Ala Phe Ser Ala Thr
    130                 135                 140

Gly Ala Leu Glu Gly Gln Met Phe Arg Lys Thr Gly Arg Leu Ile Ser
145                 150                 155                 160

Leu Ser Glu Gln Asn Leu Val Asp Cys Ser Gly Pro Gln Gly Asn Glu
                165                 170                 175

Gly Cys Asn Gly Gly Leu Met Asp Tyr Ala Phe Gln Tyr Val Gln Asp
            180                 185                 190

Asn Gly Gly Leu Asp Ser Glu Glu Ser Tyr Pro Tyr Glu Ala Thr Glu
        195                 200                 205

```
Glu Ser Cys Lys Tyr Asn Pro Lys Tyr Ser Val Ala Asn Asp Thr Gly
            210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Gly Tyr Gly Phe Glu Ser Thr
        275                 280                 285

Glu Ser Asp Asn Asn Lys Tyr Trp Leu Val Lys Asn Ser Trp Gly Glu
    290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330
```

<210> SEQ ID NO 14
<211> LENGTH: 316
<212> TYPE: PRT
<213> ORGANISM: Homo sapiens

<400> SEQUENCE: 14

```
Thr Leu Thr Phe Asp His Ser Leu Glu Ala Gln Trp Thr Lys Trp Lys
1               5                   10                  15

Ala Met His Asn Arg Leu Tyr Gly Met Asn Glu Glu Gly Trp Arg Arg
            20                  25                  30

Ala Val Trp Glu Lys Asn Met Lys Met Ile Glu Leu His Asn Gln Glu
        35                  40                  45

Tyr Arg Glu Gly Lys His Ser Phe Thr Met Ala Met Asn Ala Phe Gly
    50                  55                  60

Asp Met Thr Ser Glu Glu Phe Arg Gln Val Met Asn Gly Phe Gln Asn
65                  70                  75                  80

Arg Lys Pro Arg Lys Gly Lys Val Phe Gln Glu Pro Leu Phe Tyr Glu
                85                  90                  95

Ala Pro Arg Ser Val Asp Trp Arg Glu Lys Gly Tyr Val Thr Pro Val
            100                 105                 110

Lys Asn Gln Gly Gln Cys Gly Ser Cys Trp Ala Phe Ser Ala Thr Gly
        115                 120                 125

Ala Leu Glu Gly Gln Met Phe Arg Lys Thr Gly Arg Leu Ile Ser Leu
    130                 135                 140

Ser Glu Gln Asn Leu Val Asp Cys Ser Gly Pro Gln Gly Asn Glu Gly
145                 150                 155                 160

Cys Asn Gly Gly Leu Met Asp Tyr Ala Phe Gln Tyr Val Gln Asp Asn
                165                 170                 175

Gly Gly Leu Asp Ser Glu Glu Ser Tyr Pro Tyr Glu Ala Thr Glu Glu
            180                 185                 190

Ser Cys Lys Tyr Asn Pro Lys Tyr Ser Val Ala Asn Asp Thr Gly Phe
        195                 200                 205

Val Asp Ile Pro Lys Gln Glu Lys Ala Leu Met Lys Ala Val Ala Thr
    210                 215                 220

Val Gly Pro Ile Ser Val Ala Ile Asp Ala Gly His Glu Ser Phe Leu
225                 230                 235                 240

Phe Tyr Lys Glu Gly Ile Tyr Phe Glu Pro Asp Cys Ser Ser Glu Asp
```

```
                    245                 250                 255
Met Asp His Gly Val Leu Val Gly Tyr Gly Phe Glu Ser Thr Glu
            260                 265                 270

Ser Asp Asn Asn Lys Tyr Trp Leu Val Lys Asn Ser Trp Gly Glu
            275                 280                 285

Trp Gly Met Gly Gly Tyr Val Lys Met Ala Lys Asp Arg Arg Asn His
            290                 295                 300

Cys Gly Ile Ala Ser Ala Ala Ser Tyr Pro Thr Val
305                 310                 315

<210> SEQ ID NO 15
<211> LENGTH: 220
<212> TYPE: PRT
<213> ORGANISM: Homo sapiens

<400> SEQUENCE: 15

Ala Pro Arg Ser Val Asp Trp Arg Glu Lys Gly Tyr Val Thr Pro Val
1               5                   10                  15

Lys Asn Gln Gly Gln Cys Gly Ser Cys Trp Ala Phe Ser Ala Thr Gly
                20                  25                  30

Ala Leu Glu Gly Gln Met Phe Arg Lys Thr Gly Arg Leu Ile Ser Leu
            35                  40                  45

Ser Glu Gln Asn Leu Val Asp Cys Ser Gly Pro Gln Gly Asn Glu Gly
    50                  55                  60

Cys Asn Gly Gly Leu Met Asp Tyr Ala Phe Gln Tyr Val Gln Asp Asn
65                  70                  75                  80

Gly Gly Leu Asp Ser Glu Glu Ser Tyr Pro Tyr Glu Ala Thr Glu Glu
                85                  90                  95

Ser Cys Lys Tyr Asn Pro Lys Tyr Ser Val Ala Asn Asp Thr Gly Phe
                100                 105                 110

Val Asp Ile Pro Lys Gln Glu Lys Ala Leu Met Lys Ala Val Ala Thr
            115                 120                 125

Val Gly Pro Ile Ser Val Ala Ile Asp Ala Gly His Glu Ser Phe Leu
130                 135                 140

Phe Tyr Lys Glu Gly Ile Tyr Phe Glu Pro Asp Cys Ser Ser Glu Asp
145                 150                 155                 160

Met Asp His Gly Val Leu Val Val Gly Tyr Gly Phe Glu Ser Thr Glu
                165                 170                 175

Ser Asp Asn Asn Lys Tyr Trp Leu Val Lys Asn Ser Trp Gly Glu Glu
                180                 185                 190

Trp Gly Met Gly Gly Tyr Val Lys Met Ala Lys Asp Arg Arg Asn His
            195                 200                 205

Cys Gly Ile Ala Ser Ala Ala Ser Tyr Pro Thr Val
            210                 215                 220

<210> SEQ ID NO 16
<211> LENGTH: 175
<212> TYPE: PRT
<213> ORGANISM: Homo sapiens

<400> SEQUENCE: 16

Ala Pro Arg Ser Val Asp Trp Arg Glu Lys Gly Tyr Val Thr Pro Val
1               5                   10                  15

Lys Asn Gln Gly Gln Cys Gly Ser Cys Trp Ala Phe Ser Ala Thr Gly
                20                  25                  30

Ala Leu Glu Gly Gln Met Phe Arg Lys Thr Gly Arg Leu Ile Ser Leu
```

```
                   35                  40                  45
Ser Glu Gln Asn Leu Val Asp Cys Ser Gly Pro Gln Gly Asn Glu Gly
    50                  55                  60

Cys Asn Gly Gly Leu Met Asp Tyr Ala Phe Gln Tyr Val Gln Asp Asn
65                  70                  75                  80

Gly Gly Leu Asp Ser Glu Glu Ser Tyr Pro Tyr Glu Ala Thr Glu Glu
                85                  90                  95

Ser Cys Lys Tyr Asn Pro Lys Tyr Ser Val Ala Asn Asp Thr Gly Phe
            100                 105                 110

Val Asp Ile Pro Lys Gln Glu Lys Ala Leu Met Lys Ala Val Ala Thr
        115                 120                 125

Val Gly Pro Ile Ser Val Ala Ile Asp Ala Gly His Glu Ser Phe Leu
    130                 135                 140

Phe Tyr Lys Glu Gly Ile Tyr Phe Glu Pro Asp Cys Ser Ser Glu Asp
145                 150                 155                 160

Met Asp His Gly Val Leu Val Val Gly Tyr Gly Phe Glu Ser Thr
                165                 170                 175

<210> SEQ ID NO 17
<211> LENGTH: 42
<212> TYPE: PRT
<213> ORGANISM: Homo sapiens

<400> SEQUENCE: 17

Asn Asn Lys Tyr Trp Leu Val Lys Asn Ser Trp Gly Glu Glu Trp Gly
1               5                   10                  15

Met Gly Gly Tyr Val Lys Met Ala Lys Asp Arg Arg Asn His Cys Gly
                20                  25                  30

Ile Ala Ser Ala Ala Ser Tyr Pro Thr Val
            35                  40
```

TREATMENT OF NEURONAL CEROID LIPOFUSCINOSIS

REFERENCE TO SEQUENCE LISTING SUBMITTED ON COMPUTER

The content of the ASCII text file of the sequence listing named "eolf-othd_seq-listing.txt" which was filed in PCT/EP2019/061140 on May 1, 2019, downloaded from the WIPO database, is 44 kb in size with a created date of Nov. 2, 2020, and electronically submitted via EFS-Web herewith the application, is incorporated herein by reference in its entirety.

FIELD OF THE INVENTION

The present invention relates to the field of therapy of disorders characterized by defective enzyme activity. In particular the present invention relates to therapeutic approaches that address Neuronal Ceroid Lipofuscinosis (NCL) and a number of other diseases and conditions by means of enzyme replacement therapy.

BACKGROUND OF THE INVENTION

Many neurodegenerative disorders are associated with a lack of proteolytic capacity of the lysosomal compartment. Neuronal Ceroid Lipofuscinosis (NCL) is a group of related disorders exemplary thereof. NCL leads to early blindness and a severe progressive neurodegeneration. Cathepsin-D deficiency (CLN10 disease) leads to the most severe form of the disease.

The neuronal ceroid lipofuscinoses (NCL or CLN, listed in the "Online Mendelian Inheritance in Man" OMIM #256730) are a group of fatal inherited neurodegenerative disorders grouped by the similarity of symptoms and pathologies. Different forms of NCL are caused by mutations in at least 14 genes (Table 1).

Clinically these disorders are usually characterized by visual failure, refractory epilepsy and declines in motor and cognitive abilities leading to premature death. They are considered the most common inherited neurodegenerative disorder of childhood although the age of onset, the order of symptoms and the rapidity of disease progression may vary depending on the NCL subtype. At present there is no curative or disease-modifying treatment available. Cathepsin D (CTSD) deficiency in humans underlies the congenital form (CLN10 MIM610127) of NCL, representing the earliest and most severe variant with onset before or around birth.

Despite this variability, all NCL forms share unifying pathomorphological features, including selective damage and loss of neurons in the retina and the brain, neuroinflammation and accumulation of autofluorescent storage material-ceroid-lipofuscin. Autophagy deregulation has recently been recognized as an additional NCL hallmark. Autophagic perturbations, such as accumulated autophagosomes and autophagic substrates, have been identified in several CLN mouse models, pointing to a possible blockage in the autophagic flux (Table 1). This suggests that autophagic perturbations may play a central role in the aetiology of NCL and that tackling these perturbations may be an efficient therapeutic avenue.

TABLE 1

Overview of gene mutations, gene products and clinical phenotypes in different NCL disorders. Disorders with proven autophagic perturbations are highlighted in bold.

| Locus Name | Gene | Protein | Clinical Phenotype |
|---|---|---|---|
| CLN1 | PPT1 | Palmitoyl-protein thioesterase 1 (PPT-1) | Infantile classic, late infantile, juvenile, adult |
| CLN2 | TPP1 | Tripeptidyl-peptidase 1 (TPP-1) | Late infantile classic, juvenile |
| CLN3 | CLN3 | CLN3 | Juvenile classic |
| CLN4 | DNAJC5 | DNAJC5 | Adult autosomal dominant |
| CLN5 | CLN5 | Lysosomal matrix protein | Late infantile variant, juvenile, adult |
| CLN6 | CLN6 | Membrane protein | Late infantile variant, adult (Kufs type A) |
| CLN7 | MFSD8 | MFSD8 | Late infantile variant, juvenile, adult |
| CLN8 | CLN8 | Membrane protein | Late infantile variant, progressive epilepsy with mental retardation |
| CLN9 | Unknown | Unknown | Juvenile |
| CLN10 | CTSD | Cathepsin-D (CTSD) | Congenital classic, late infantile, adult |
| CLN11 | GRN | Progranulin (GRN) | Adult |
| CLN12 | ATP13A2 | ATPase type 13A2 | Juvenile, Kufor-Raheb syndrome |
| CLN13 | CTSF | Cathepsin-F | Adult Kufs type |
| CLN14 | KCTD7 | Potassium channel tetrameristion domain-containing protein 7 (KCTD7) | Infantile, progressive myoclonus epilepsy 3 |

In view of the lack of any satisfactory treatment of NCL, there is a strong need for providing means to treat the disease or at least alleviate the symptoms of the disease. The current economic burden for each NCL patient is considerable (estimated >1 mio USD per year per patient). Most patients require lifelong care and frequent medical attention. An early initiated and effective therapy would reduce these costs considerably and would radically improve the quality of life of the patients and their families.

Synucleinopathies are neurodegenerative diseases, which similarly to NCL are characterised by the abnormal accumulation of protein aggregates, namely alpha-synuclein aggregation in neurons, nerve fibres or glial cells. There are three main types of synucleinopathy, Parkinson's disease, dementia with Lewy bodies (including certain Alzheimer's disease variants), and multiple system atrophy. Some rare disorders, such as various neuroaxonal dystrophies, also have α-synuclein pathologies.

A certain overlap exists with diseases characterized by a block or impairment of autophagic flux, i.e. diseases where the organism's capability of degrading long-lived proteins, misfolded proteins and impaired cytoplasmic organelles is impaired. Examples of diseases characterized by block/impairment of autophagic flow are Alzheimer's disease, amyotrophic lateral sclerosis, Huntington's disease, Parkinson's disease and different types of lysosomal storage disorders.

These diseases share the features of parkinsonism, impaired cognition, sleep disorders, and visual hallucinations. Further, satisfactory treatments of each of these diseases are still lacking.

OBJECTS OF EMBODIMENTS OF THE INVENTION

It is an object of embodiments of the invention to provide methods and agents that are capable of treating or alleviating symptoms of NCL. It is a further object to provide similar treatments of diseases that—as is the case of NCL—are characterized by protein aggregate formation or block in autophagic flow.

SUMMARY OF THE INVENTION

The present inventors have set out to develop and perform preclinical and clinical trials using a recombinant protease (initially human pro-Cathepsin-D, rhproCTSD, but also human pro-Cathepsin-B, rhproCTSB, and human pro-Cathepsin, rhproCTSL) as a therapeutic drug in patients with the rare inherited disease NCL for which no treatment is currently available, and also for a number of other diseases, cf. above.

The inventors have for this purpose engineered human recombinant pro-cathepsin-D and pro-cathepsin-B and have now, as will be apparent from the examples, established Proof-of-Principle of endocytosis of the exogenously administered rhproCTSD and rhproCTSB to mammalian tissue cells (liver, spleen, kidney and muscle) and delivery to the lysosome, enzyme activity in vitro and in vivo and after cellular uptake, it has been shown that rhproCTSB and rhproCTSD provides for clearance of relevant substrates in the cells (e.g. liver and spleen) and partial rescue of autophagic block in different body tissues. Since the recombinant enzyme is provided as the inactive proenzyme, it is only proteolytically activated upon cellular uptake and delivery to lysosomes. The recombinant enzymes further exhibit a prolonged shelf and tissue half-life.

In particular, it has been demonstrated by the inventors that the recombinant pro-cathepsin-D is taken up and successfully delivered to lysosomes in cells and in a murine disease model. Dosing in cathepsin-D knockout mice leads to a correction of many of the pathological manifestations of NCL. Preliminary cell-based results suggest that the presently presented therapeutic approach may also be effective in clearing protein aggregates in other types of NCL.

In a mouse disease model it has also been demonstrated that the enzyme elicits the substrate reduction in relevant tissues and methods to demonstrate enzyme uptake across the Blood-Brain Barrier have been and are being investigated. The enzyme produced is of human origin, meaning that the risk of adverse effects due to immunological rejection reactions is minimal.

In summary, the proof-of-principle experiments provide evidence that an in vivo application of a recombinant cathepsin-D protease leads to a correction of lysosomal protein storage (as in cathepsin-D deficiency, CLN10). Further, preliminary results implies that in vivo application of recombinant cathepsin-B is an equally feasible therapeutic agent.

So, in a first aspect the present invention relates to a method of therapeutic and/or prophylactic treatment of a human being for a Neuronal Ceroid Lipofuscinosis (NCL) or synucleinopathy or disease characterized by block of autophagic flow comprising administration to the human being of a pharmaceutically effective and acceptable amount of pro-cathepsin D (proCTSD) and/or pro-cathepsin B (proCTSB), wherein said proCTSD comprises an amino acid sequence comprising at most 20 amino acid substitutions and/or at most 20 amino acid deletions compared SEQ ID NO: 3, wherein said proCTSB comprises an amino acid sequence comprising at most 20 amino acid substitutions and/or at most 20 amino acid deletions compared to SEQ ID NO: 9, and wherein said proCTSL comprises an amino acid sequence comprising at most 20 amino acid substitutions and/or at most 20 amino acid deletions compared to SEQ ID NO: 14.

In a second aspect, the present invention relates to human pro-cathepsin D (proCTSD), which comprises an amino acid sequence comprising at most 20 amino acid substitutions and/or and or at most 20 amino acid deletions compared SEQ ID NO: 3, for use in a method of therapeutic and/or prophylactic treatment of NCL or synucleinopathy or a disease characterized by block of autophagic flow. Also, the present invention in a separate third aspect relates to pro-cathepsin B (proCTSB), which comprises an amino acid sequence comprising at most 20 amino acid substitutions and/or at most 20 amino acid deletions compared SEQ ID NO: 9, for use in a method of therapeutic and/or prophylactic treatment of NCL or synucleinopathy or a disease characterized by block of autophagic flow. Also, the present invention in a separate 4$^{th}$ aspect relates to pro-cathepsin L (proCTSL), which comprises an amino acid sequence comprising at most 20 amino acid substitutions and/or at most 20 amino acid deletions compared SEQ ID NO: 14, for use in a method of therapeutic and/or prophylactic treatment of NCL or synucleinopathy or a disease characterized by block of autophagic flow.

LEGENDS TO THE FIGURE

FIG. 1: Treatment with rhproCTSD corrects visceral abnormalities in CTSD-deficient mice.

Panel A: Immunoblot of liver of P23 CTSD$^{-/-}$ mice treated with rhproCTSD and age-matched PBS-injected controls.

Panel B: Liver sections of P23 CTSD-/- mice treated with rhproCTSD and age-matched PBS-injected controls analyzed by light microscopy. White arrows indicate cellular pathology and vacuolization which is completely corrected after replacement of cathepsin-D.

Panel C: Quantification of LC3-II levels (relative to loading control GAPDH) in immunoblot of spleen of P23 CTSD$^{-/-}$ mice treated with rhproCTSD (n=5) and age-matched PBS-injected controls (n=3). Data were analyzed by unpaired t-test. ** $p<0.01$. Error bars represent the standard deviation.

Figure 2:
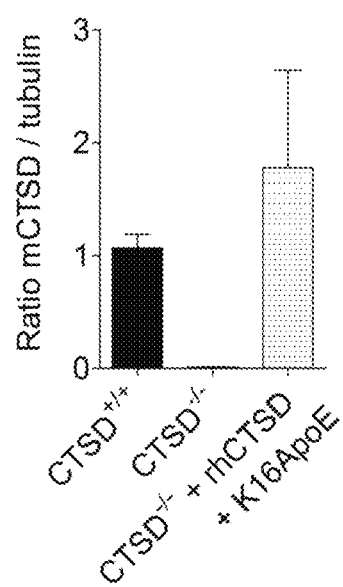

FIG. 2 Mature CTSD levels after co-injection of rhproCTSD and K16ApoE in the brain of CTSD$^{-/-}$ mice. Quantification of mature CTSD levels (relative to loading control tubulin) in immunoblot of brain of P21 CTSD$^{-/-}$ mice 24 h after I.V. injection of 86 mg/Kg rhproCTSD and 40 nmol K16ApoE and age-matched PBS-injected controls. The error bars represent the standard deviation of technical duplicates.

Figure 3:
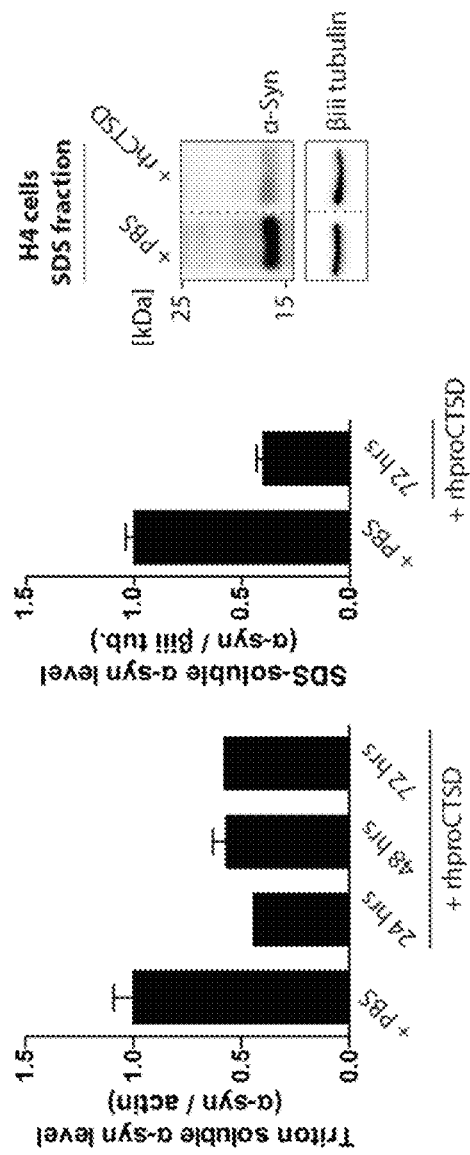

FIG. 3: α-Synuclein-overexpressing human H4 cells were treated with rhproCTSD for 24-72 hours. Cells were lysed with Triton buffer and insoluble fractions were further lysed in SDS buffer. Soluble and insoluble lysates were blotted and stained for α-Synuclein (C20 antibody). A: Soluble α-Synuclein signal was quantified and normalized to loading control (actin) n=1-2. B: SDS-soluble lysate was also quantified and normalized to βiii tubulin.

C: Immunoblot of α-Synuclein (C20 antibody) of SDS-soluble H4 cell lysates indicating a decrease of ~17 kDa-sized α-synuclein after rhproCTSD treatment for 72 hours (n=2).

Figure 4:
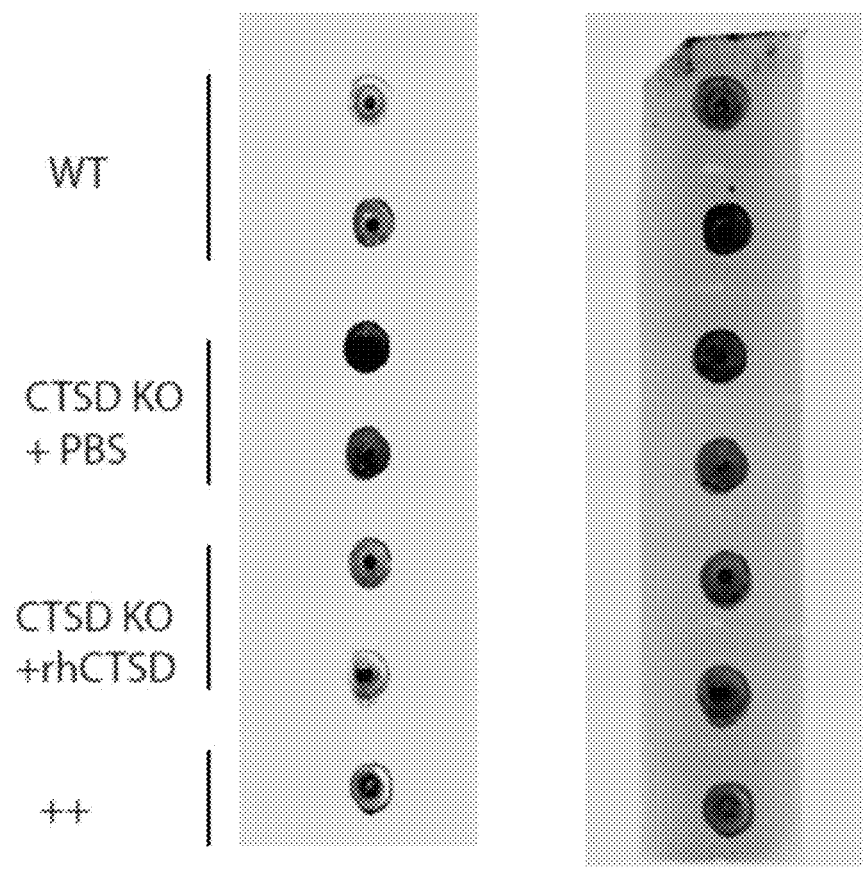

FIG. 4: Dot blots showing expression levels of α-synuclein in lysates from murine brains. The "MJFR synuclein Ab" panel shows dot blots for antibody reactivity of brain lysates from wild-type ("WT") mice, 23 days old CTSD knock-out mice after intracranial injection of PBS ("CTSD KO+PBS"), 23 days old CTSD knock-out mice after intracranial injection of rhCTSD ("CTSD KO+rhCTSD") and 30 days old long-term survival CTSD knock-out mice after intracranial injection of rhCTSD ("++").

DETAILED DISCLOSURE OF THE INVENTION

Definitions

"Cathepsin D" is in the present context a common name for all forms—including the pre-pro-form, the pro-form, the intermediate active and the mature form of human Cathepsin D. The amino acid sequence of the pre-pro-form is exemplified by SEQ ID NO: 2:

```
                                        (SEQ ID NO: 2)
MQPSSLLPLA LCLLAAPASA LVRIPLHKFT SIRRTMSEVG

GSVEDLIAKG PVSKYSQAVP AVTEGPIPEV LKNYMDAQYY

GEIGIGTPPQ CFTVVFDTGS SNLWVPSIHC KLLDIACWIH

HKYNSDKSST YVKNGTSFDI HYGSGSLSGY LSQDTVSVPC

QSASSASALG GVKVERQVFG EATKQPGITF IAAKFDGILG

MAYPRISVNN VLPVFDNLMQ QKLVDQNIFS FYLSRDPDAQ

PGGELMLGGT DSKYYKGSLS YLNVTRKAYW QVHLDQVEVA

SGLTLCKEGC EAIVDTGTSL MVGPVDEVRE LQKAIGAVPL

IQGEYMIPCE KVSTLPAITL KLGGKGYKLS PEDYTLKVSQ

AGKTLCLSGF MGMDIPPPSG PLWILGDVFI GRYYTVFDRD

NNRVGFAEAA RL
```

The human cathepsin D pro-protein (proCTSD) is exemplified by the amino acid sequence SEQ ID NO: 3 (i.e. SEQ ID NO: 2, residues 21-412):

```
                                        (SEQ ID NO: 3)
LVRIPLHKFT SIRRTMSEVG GSVEDLIAKG PVSKYSQAVP

AVTEGPIPEV LKNYMDAQYY GEIGIGTPPQ CFTVVFDTGS

SNLWVPSIHC KLLDIACWIH HKYNSDKSST YVKNGTSFDI

HYGSGSLSGY LSQDTVSVPC QSASSASALG GVKVERQVFG

EATKQPGITF IAAKFDGILG MAYPRISVNN VLPVFDNLMQ

QKLVDQNIFS FYLSRDPDAQ PGGELMLGGT DSKYYKGSLS

YLNVTRKAYW QVHLDQVEVA SGLTLCKEGC EAIVDTGTSL

MVGPVDEVRE LQKAIGAVPL IQGEYMIPCE KVSTLPAITL

KLGGKGYKLS PEDYTLKVSQ AGKTLCLSGF MGMDIPPPSG

PLWILGDVFI GRYYTVFDRD NNRVGFAEAA RL
```

The intermediate (active) form of human cathepsin D (iCTSD) is exemplified by the amino acid sequence SEQ ID NO: 4 (i.e. SEQ ID NO: 2, residues 65-412):

```
                                        (SEQ ID NO: 4)
GPIPEV LKNYMDAQYY GEIGIGTPPQ CFTVVFDTGS SNLWVPSIHC

KLLDIACWIH HKYNSDKSST YVKNGTSFDI HYGSGSLSGY

LSQDTVSVPC QSASSASALG GVKVERQVFG EATKQPGITF

IAAKFDGILG MAYPRISVNN VLPVFDNLMQ QKLVDQNIFS

FYLSRDPDAQ PGGELMLGGT DSKYYKGSLS YLNVTRKAYW

QVHLDQVEVA SGLTLCKEGC EAIVDTGTSL MVGPVDEVRE

LQKAIGAVPL IQGEYMIPCE KVSTLPAITL KLGGKGYKLS

PEDYTLKVSQ AGKTLCLSGF MGMDIPPPSG PLWILGDVFI

GRYYTVFDRD NNRVGFAEAA RL
```

Finally, the mature form of human cathepsin D (mCTSD) is exemplified by the disulphide-linked heterodimer constituted by SEQ ID NOs: 5 and 6 (i.e. SEQ ID NO: 2, residues 65-162 and 169-412), respectively:

```
                                        (SEQ ID NO: 5)
GPIPEV LKNYMDAQYY GEIGIGTPPQ CFTVVFDTGS SNLWVPSIHC

KLLDIACWIH HKYNSDKSST YVKNGTSFDI HYGSGSLSGY

LSQDTVSVPC QS
```

```
                                        (SEQ ID NO: 6)
LG GVKVERQVFG EATKQPGITF IAAKFDGILG MAYPRISVNN

VLPVFDNLMQ QKLVDQNIFS FYLSRDPDAQ PGGELMLGGT

DSKYYKGSLS YLNVTRKAYW QVHLDQVEVA SGLTLCKEGC

EAIVDTGTSL MVGPVDEVRE LQKAIGAVPL IQGEYMIPCE

KVSTLPAITL KLGGKGYKLS PEDYTLKVSQ AGKTLCLSGF

MGMDIPPPSG PLWILGDVFI GRYYTVFDRD NNRVGFAEAA RL
```

The full-length human pre-pro-protein is i.a. encoded by the following DNA sequence (SEQ ID NO: 1) but due to the genetic code degeneracy, numerous alternative DNA sequences encode the same protein.

```
                                        (SEQ ID NO: 1)
atgcagccct ccagccttct gccgctcgcc ctctgcctgc tggctgcacc cgcctccgcg ctcgtcagga tcccgctgca caagttcacg tccatccgcc ggaccatgtc ggaggttggg ggctctgtgg aggacctgat tgccaaaggc cccgtctcaa agtactccca ggcggtgcca gccgtgaccg aggggcccat tcccgaggtg ctcaagaact acatggacgc ccagtactac ggggagattg gcatcgggac gccccccag tgcttcacag tcgtcttcga cacgggctcc tccaacctgt gggtccctc catccactgc aaactgctgg acatcgcttg ctggatccac cacaagtaca acagcgacaa gtccagcacc tacgtgaaga atggtacctc gtttgacatc cactatggct cgggcagcct ctccgggtac ctgagccagg acactgtgtc ggtgccctgc cagtcagcgt cgtcagcctc tgccctgggc ggtgtcaaag tggagaggca ggtctttggg gaggccacca agcagccagg catcaccttc atcgcagcca agttcgatgg catcctgggc atggcctacc cccgcatctc cgtcaacaac gtgctgcccg
```

```
-continued
tcttcgacaa cctgatgcag cagaagctgg tggaccagaa catcttctcc ttctacctga gcagggaccc agatgcgcag cctggggtg agctgatgct gggtggcaca gactccaagt attacaaggg ttctctgtcc tacctgaatg tcaccgcaa ggcctactgg caggtccacc tggaccaggt ggaggtggcc agcgggctga ccctgtgcaa ggagggctgt gaggccattg tggacacagg cacttccctc atggtgggcc cggtggatga ggtgcgcgag ctgcagaagg ccatcggggc cgtgccgctg attcagggcg agtacatgat ccctgtgag aaggtgtcca ccctgcccgc gatcacactg aagctgggag gcaaaggcta caagctgtcc ccagaggact acacgctcaa ggtgtcgcag gccgggaaga ccctctgcct gagcggcttc atgggcatgg acatcccgcc acccagcggg ccactctgga tcctgggcga cgtcttcatc ggccgctact acactgtgtt tgaccgtgac aacaacaggg tgggcttcgc cgaggctgcc cgcctctag
```

"Human pro-Cathepsin D" (proCTSD) is thus the biologically inactive pro-form of biologically active Cathepsin-D and it is exemplified by SEQ ID NO: 3. However, since there exists a natural sequence variation in the amino acid sequence of pro-Cathepsin D in humans, and since not all sequence variants are associated with the diseases discussed herein, it will be understood that non-disease related sequence variants of SEQ ID NO: 3 that are converted to an active form exhibiting Cathepsin D activity are also included within the meaning of the term proCTSD. In the present disclosure, the terms "rhproCTSD" is used for a recombinant form of human pro-Cathepsin D, cf. the examples.

"Cathepsin B" is in the present context a common name for all forms—including the pre-pro-form, the pro-form, the single chain mature and the two chain mature forms of human Cathepsin B. The amino acid sequence of the pre-pro-form is exemplified by SEQ ID NO: 8:

```
                                    (SEQ ID NO: 8)
MWQLWASLCC LLVLANARSR PSFHPLSDEL VNYVNKRNTT

WQAGHNFYNV DMSYLKRLCG TFLGGPKPPQ RVMFTEDLKL

PASFDAREQW PQCPTIKEIR DQGSCGSCWA FGAVEAISDR

ICIHTNAHVS VEVSAEDLLT CCGSMCGDGC NGGYPAEAWN

FWTRKGLVSG GLYESHVGCR PYSIPPCEHH VNGSRPPCTG

EGDTPKCSKI CEPGYSPTYK QDKHYGYNSY SVSNSEKDIM

AEIYKNGPVE GAFSVYSDFL LYKSGVYQHV TGEMMGGHAI

RILGWGVENG TPYWLVANSW NTDWGDNGFF KILRGQDHCG

IESEVVAGIP RTDQYWEKI
```

The human cathepsin B pro-protein (proCTSB) is exemplified by the amino acid sequence SEQ ID NO: 9 (i.e. SEQ ID NO: 8, residues 18-339):

```
                                    (SEQ ID NO: 9)
RSR PSFHPLSDEL VNYVNKRNTT WQAGHNFYNV DMSYLKRLCG

TFLGGPKPPQ RVMFTEDLKL PASFDAREQW PQCPTIKEIR
```

```
-continued
DQGSCGSCWA FGAVEAISDR ICIHTNAHVS VEVSAEDLLT

CCGSMCGDGC NGGYPAEAWN FWTRKGLVSG GLYESHVGCR

PYSIPPCEHH VNGSRPPCTG EGDTPKCSKI CEPGYSPTYK

QDKHYGYNSY SVSNSEKDIM AEIYKNGPVE GAFSVYSDFL

LYKSGVYQHV TGEMMGGHAI RILGWGVENG TPYWLVANSW

NTDWGDNGFF KILRGQDHCG IESEVVAGIP RTDQYWEKI
```

The single chain mature form (active) form of human cathepsin B (scmCTSB) is exemplified by the amino acid sequence SEQ ID NO: 10 (i.e. SEQ ID NO: 8, residues 80-333):

```
                                    (SEQ ID NO: 10)
L PASFDAREQW PQCPTIKEIR DQGSCGSCWA FGAVEAISDR

ICIHTNAHVS VEVSAEDLLT CCGSMCGDGC NGGYPAEAWN

FWTRKGLVSG GLYESHVGCR PYSIPPCEHH VNGSRPPCTG

EGDTPKCSKI CEPGYSPTYK QDKHYGYNSY SVSNSEKDIM

AEIYKNGPVE GAFSVYSDFL LYKSGVYQHV TGEMMGGHAI

RILGWGVENG TPYWLVANSW NTDWGDNGFF KILRGQDHCG

IESEVVAGIP RTD
```

Finally, the two chain mature form of human cathepsin B (tcmCTSB) is exemplified by the disulphide-linked heterodimer constituted by SEQ ID NOs: 11 and 12 (i.e. SEQ ID NO: 8, residues 80-126 and 129-333), respectively:

```
                                    (SEQ ID NO: 11)
L PASFDAREQW PQCPTIKEIR DQGSCGSCWA FGAVEAISDR

ICIHTN (SEQ ID NO: 12)
VS VEVSAEDLLT CCGSMCGDGC NGGYPAEAWN FWTRKGLVSG

GLYESHVGCR PYSIPPCEHH VNGSRPPCTG EGDTPKCSKI

CEPGYSPTYK QDKHYGYNSY SVSNSEKDIM AEIYKNGPVE

GAFSVYSDFL LYKSGVYQHV TGEMMGGHAI RILGWGVENG

TPYWLVANSW NTDWGDNGFF KILRGQDHCG IESEVVAGIP RTD
```

The full-length human pre-pro-protein for CTSB is i.a. encoded by the following DNA sequence (SEQ ID NO: 7) but due to the genetic code degeneracy, numerous alternative DNA sequences encode the same protein.

```
                                    (SEQ ID NO: 7)
atgtggcagc tctgggcctc cctctgctgc ctgctggtgt tggccaatgc ccggagcagg ccctctttcc atcccctgtc ggatgagctg gtcaactatg tcaacaaacg gaataccacg tggcaggccg ggcacaactt ctacaacgtg gacatgagct acttgaagag gctatgtggt accttcctgg gtgggcccaa gccacccag agagttatgt ttaccgagga cctgaagctg cctgcaagct tcgatgcacg ggaacaatgg ccacagtgtc
```

```
                -continued
ccaccatcaa agagatcaga gaccagggct cctgtggctc ctgctgggcc ttcggggctg tggaagccat ctctgaccgg atctgcatcc acaccaatgc gcacgtcagc gtggaggtgt cggcggagga cctgctcaca tgctgtggca gcatgtgtgg ggacggctgt aatggtggct atcctgctga agcttggaac ttctggacaa gaaaaggcct ggtttctggt ggcctctatg aatccatgt agggtgcaga ccgtactcca tccctccctg tgagcaccac gtcaacggct cccggccccc atgcacgggg gagggagata cccccaagtg tagcaagatc tgtgagcctg gctacagccc gacctacaaa caggacaagc actacggata caattcctac agcgtctcca atagcgagaa ggacatcatg gccgagatct acaaaaacgg ccccgtggag ggagctttct ctgtgtattc ggacttcctg ctctacaagt caggagtgta ccaacacgtc accggagaga tgatgggtgg ccatgccatc cgcatcctgg gctggggagt ggagaatggc acaccctact ggctggttgc caactcctgg aacactgact ggggtgacaa tggcttcttt aaaatactca gaggacagga tcactgtgga atcgaatcag aagtggtggc tggaattcca cgcaccgatc agtactggga aaagatctaa
```

"Human pro-Cathepsin B" (proCTSB) is thus the biologically inactive pro-form of biologically active Cathepsin-B and it is exemplified by SEQ ID NO: 9. However, since there exists a natural sequence variation in the amino acid sequence of pro-Cathepsin B in humans, and since not all sequence variants are associated with the diseases discussed herein, it will be understood that non-disease related sequence variants of SEQ ID NO: 9 that are converted to an active form exhibiting Cathepsin B activity are also included within the meaning of the term proCTSB. In the present disclosure, the terms "rhproCTSB" is used for a recombinant form of human pro-Cathepsin B, cf. the examples.

"Cathepsin L" is in the present context a common name for all forms—including the pre-pro-form, the pro-form, the intermediate active and the mature form of human Cathepsin L. The amino acid sequence of the pre-pro-form is exemplified by SEQ ID NO: 13:

```
                                        (SEQ ID NO: 13)
MNPTLILAAF CLGIASATLT FDHSLEAQWT KWKAMHNRLY

GMNEEGWRRA VWEKNMKMIE LHNQEYREGK HSFTMAMNAF

GDMTSEEFRQ VMNGFQNRKP RKGKVFQEPL FYEAPRSVDW

REKGYVTPVK NQGQCGSCWA FSATGALEGQ MFRKTGRLIS

LSEQNLVDCS GPQGNEGCNG GLMDYAFQYV QDNGGLDSEE

SYPYEATEES CKYNPKYSVA NDTGFVDIPK QEKALMKAVA

TVGPISVAID AGHESFLFYK EGIYFEPDCS SEDMDHGVLV

VGYGFESTES DNNKYWLVKN SWGEEWGMGG YVKMAKDRRN

HCGIASAASY PTV
```

The human cathepsin L pro-protein (proCTSL) is exemplified by the amino acid sequence SEQ ID NO: 14 (i.e. SEQ ID NO: 13, residues 18-333):

```
                                        (SEQ ID NO: 14)
TLT FDHSLEAQWT KWKAMHNRLY GMNEEGWRRA VWEKNMKMIE

LHNQEYREGK HSFTMAMNAF GDMTSEEFRQ VMNGFQNRKP

RKGKVFQEPL FYEAPRSVDW REKGYVTPVK NQGQCGSCWA

FSATGALEGQ MFRKTGRLIS LSEQNLVDCS GPQGNEGCNG

GLMDYAFQYV QDNGGLDSEE SYPYEATEES CKYNPKYSVA

NDTGFVDIPK QEKALMKAVA TVGPISVAID AGHESFLFYK

EGIYFEPDCS SEDMDHGVLV VGYGFESTES DNNKYWLVKN

SWGEEWGMGG YVKMAKDRRN HCGIASAASY PTV
```

The intermediate (active) form of human cathepsin L (iCTSL) is exemplified by the amino acid sequence SEQ ID NO: 15 (i.e. SEQ ID NO: 13, residues 114-333):

```
                                        (SEQ ID NO: 15)
APRSVDW REKGYVTPVK NQGQCGSCWA FSATGALEGQ

MFRKTGRLIS LSEQNLVDCS GPQGNEGCNG GLMDYAFQYV

QDNGGLDSEE SYPYEATEES CKYNPKYSVA NDTGFVDIPK

QEKALMKAVA TVGPISVAID AGHESFLFYK EGIYFEPDCS

SEDMDHGVLV VGYGFESTES DNNKYWLVKN SWGEEWGMGG

YVKMAKDRRN HCGIASAASY PTV
```

Finally, the mature form of human cathepsin L (mCTSL) is exemplified by the disulphide-linked heterodimer constituted by SEQ ID NOs: 16 and 17 (i.e. SEQ ID NO: 13, residues 114-288 and 292-333), respectively:

```
                                        (SEQ ID NO: 16)
APRSVDW REKGYVTPVK NQGQCGSCWA FSATGALEGQ

MFRKTGRLIS LSEQNLVDCS GPQGNEGCNG GLMDYAFQYV

QDNGGLDSEE SYPYEATEES CKYNPKYSVA NDTGFVDIPK

QEKALMKAVA TVGPISVAID AGHESFLFYK EGIYFEPDCS

SEDMDHGVLV VGYGFEST (SEQ ID NO: 17)
NNKYWLVKN SWGEEWGMGG YVKMAKDRRN HCGIASAASY PTV
```

"Human pro-Cathepsin L" (proCTSL) is thus the biologically inactive pro-form of biologically active Cathepsin-L and it is exemplified by SEQ ID NO: 14. However, since there exists a natural sequence variation in the amino acid sequence of pro-Cathepsin L in humans, and since not all sequence variants are associated with the diseases discussed herein, it will be understood that non-disease related sequence variants of SEQ ID NO: 14 that are converted to an active form exhibiting Cathepsin L activity are also included within the meaning of the term proCTSL.

A "pharmaceutically effective" amount of proCTSD/proCTSB/proCTSL is in the present context an amount of a propeptide as defined above, where 1) the propeptide is posttranslationally modified to arrive at an enzymatically active Cathepsin D/B, and 2) the amount administered is effective in reducing ceroid-lipofuscin or other types of storage products (e.g. saposin C, saposin-D, subunit C of the mitochondrial ATP synthase) in the recipient's cells. It will therefore be understood that any sequence variant of SEQ ID NO: 3 or 9, which is administered, will comprise an amino acid sequence that is either A) part of a natural allelic variant (e.g. from a genetic polymorphism) of the human CTSD or CTSB gene, respectively, where the sequence variant is not itself related to NCL, or B) is a non-natural sequence variant or rare mutant, which exhibits a sufficient aspartic endoprotease activity characteristic of Cathepsin D or a sufficient cysteine endo/exo-protease activity of Cathepsin B.

"A pharmaceutically acceptable amount" has its usual meaning in the art, i.e. an amount which does not cause unacceptable adverse effects in the treated human being. For details concerning dosages in humans, cf. below.

The expression "therapeutic treatment" relates to a treatment as disclosed herein, where symptoms or signs of established disease are reduced or eliminated by the treatment.

In contrast, "prophylactic treatment" is a treatment as disclosed herein that reduces the risk in the treated individuals of developing signs and symptoms of established disease or which at least reduces the risk of developing further disease signs or symptoms than those that are already present when the treatment is instigated. Also, a treatment which at least delays the progression of a disease is in the present context considered a prophylactic treatment. It is in practice possible that a treatment can have both direct therapeutic effects and prophylactic effects also.

Specific Embodiments of the First Aspect of the Invention

As indicated above, the first aspect of the invention relates to a method of therapeutic and/or prophylactic treatment of a human being for a Neuronal Ceroid Lipofuscinosis (NCL) or synucleinopathy or disease characterized by block of autophagic flow comprising administration to the human being of a pharmaceutically effective and acceptable amount of pro-cathepsin D (proCTSD) and/or pro-cathepsin B (proCTSB), wherein said proCTSD comprises an amino acid sequence comprising at most 20 amino acid substitutions and/or at most 20 amino acid deletions compared SEQ ID NO: 3, wherein said proCTSB comprises an amino acid sequence comprising at most 20 amino acid substitutions and/or at most 20 amino acid deletions compared to SEQ ID NO: 9, and wherein said proCTSL comprises an amino acid sequence comprising at most 20 amino acid substitutions and/or at most 20 amino acid deletions compared to SEQ ID NO: 14.

The number of amino acid substitutions compared to SEQ ID NO: 3 or SEQ ID NO: 9 or SEQ ID NO: 14 in a variant sequence can be any number selected from the group consisting of 1, 2, 3, 4, 5, 6, 7, 8, 9, 10, 11, 12, 13, 14, 15, 16, 17, 18, 19, and 20 substitutions. Substitutions that are possible are in particular conservative substitutions, i.e. substitutions of an amino acid with another amino acid within the same class:

| Class | Amino acids |
|---|---|
| Aliphatic | Gly, Ala, Val, Leu, Ile |
| Aromatic | Phe, Tyr, Trp |
| Basic | His, Lys, Arg |
| Acidic/amides | Asp, Asn, Gln, Glu |

The number of amino acid deletions compared to SEQ ID NO: 3 or SEQ ID NO: 9 or SEQ ID NO: 14 in a variant sequence can be any number selected from the group consisting of 1, 2, 3, 4, 5, 6, 7, 8, 9, 10, 11, 12, 13, 14, 15, 16, 17, 18, 19, and 20 deletions.

The total number of amino acid substations and deletions compared to SEQ ID NO: 3 or SEQ ID NO: 9 or SEQ ID NO: 14 in a variant sequence can be any number selected from the group consisting of 1, 2, 3, 4, 5, 6, 7, 8, 9, 10, 11, 12, 13, 14, 15, 16, 17, 18, 19, and 20.

It is preferred not to deviate from the amino acid sequence of the most common human wildtypes of human proCTSD and proCTSB: it is well-known that even minor amino acid changes in the primary structure of a protein can render a non-immunogenic molecule immunogenic due to the emergence of MHC Class II binding peptides in the altered sequence, so administration of the most common wildtypes (SEQ ID NO: 3 and SEQ ID NO: 9 and SEQ ID NO: 14) will prevent any potential problems relating to immunoclearance of the proCTSD and/or proCTSB administered. However, in the embodiments disclosed herein where the proCTSD and/or proCTSB is administered directly to the CNS, immunoclearance constitutes a less relevant problem and in those embodiments, sequence variants of proCTSD and/or proCTSB can be employed.

At any rate, introduction of any amino acid deletion or substitution must be made with a view to preservation of biologic function, i.a. meaning that the two catalytic residues Asp-33 and Asp-231 (using the amino acid residue numbering of SEQ ID NO: 3) should be preserved, and the same is true for the highly conserved Arg-125 as well as the 8 Cys-residues that contribute to the 4 stabilising disulphide bridges in mature CTSD. Generally, introduction of any amino acid substitution or deletion into SEQ ID NO: 3 should further be made in order to not generate loss of catalytic activity—and this also means that such deletions and substitutions should not prevent the formation of the catalytically active forms for CTSD, i.e. amino acid changes introduced into SEQ ID NO: 3 should not interfere with correct processing of the proCTSD and should not prevent correct folding/assembly of the catalytic active forms. Similar considerations apply for proCTSB and proCTSL.

While the proCTSD and/or proCTSB and/or proCTSL may include additional amino acids of heterologous origin (that is, not normally associated with proCTSD/proCTSB/proCTSL), e.g. purification tags, protraction groups etc., the proCTSD and/or proCTSB and/or proCTSL administered to the patient typically does not include a signal peptide, in particular amino acid residues 1-20 of SEQ ID NO: 2 and amino acid residues 1-17 of SEQ ID NO: 8 and amino acids 1-17 of SEQ ID NO: 13. While the signal peptide may be important when recombinantly producing the peptide, its excision from the pro-protein is important for the subsequent activation of the pro-protein into the mature and active forms of CTSD and CTSB and CTSL.

As mentioned, the proCTSD and proCTSB and proCTSL may include a purification tag, such as a His tag, cf. the examples below where such a HIS tagged version is utilised. However, the preferred propeptides used in the invention will not contain such purification tags and will consist of the amino acid sequence set forth in SEQ ID NO: 3 or SEQ ID NO: 9 or SEQ ID NO: 14, or a variant of SEQ ID NO: 3 or SEQ ID NO: 9 or SEQ ID NO: 14 described above.

The proCTSD, which is administered, is preferably one that upon entry into lysosomes can be or is activated into intermediate cathepsin D (iCTSD) such as the iCTSD consisting of SEQ ID NO: 4 and/or into mature cathepsin D (mCTSD), such as the mCTSD consisting of a heterodimer of SEQ ID NO: 5 and SEQ ID NO: 6. The proCTSB, which is administered, is preferably one that upon entry into lysosomes can be activated into mature single chain cathepsin B (scmCTSB) such as the scmCTSB consisting of SEQ ID NO: 10 and/or into two chain mature cathepsin B (tcmCTSB), such as the tcmCTSB consisting of a heterodimer of SEQ ID NO: 11 and SEQ ID NO: 12. The proCTSL, which is administered, is preferably one that upon entry into lysosomes can be or is activated into intermediate cathepsin L (iCTSL) such as the iCTSL consisting of SEQ ID NO: 15 and/or into mature cathepsin L (mCTSL), such as the mCTSL consisting of a heterodimer of SEQ ID NO: 16 and SEQ ID NO: 17.

The proCTSD and/or proCTSB and/or proCTSL can be administered directly into the cerebrovascular fluid, such as via an intrathecal delivery pump. Alternatively, the proCTSD and/or proCTSB and/or proCTSL can be administered via the intraveneous or intra-arterial route; typically this requires that the proCTSD/proCTSB/proCTSL is co-administered or formulated with an agent that is capable of allowing passage of the proCTSD/proCTSB/proCTSL across the blood-brain barrier, or that the proCTSD/proCTSB/proCTSL is coupled to a moiety that has the same effect. Also, intravitreal injection of proCTSD/proCTSB/proCTSL is attractive in order to directly address retinal cells.

The maximum dosage over 24 hours is typically in the range between 0.1 and 1000 mg proCTSD or proCTSB or proCTSL per kg body weight, such as in the range between 0.5 and 500 mg, between 1.0 and 400 mg, between 2 and 300 mg, between 3 and 200 mg, between 4 and 150 mg, and between 5 and 100 mg per kg body weight per day.

In general, human dose can be calculated based on animal dosages as set out in FDA's "Guidance for Industry—Estimating the Maximum Safe Starting Dose in Initial Clinical Trials for Therapeutics in Adult Healthy Volunteers" published in July 20015. The formulas provided for establishing the maximum recommended starting dose (MRSD) provided in this document can be used also according to the present invention to estimate pharmaceutically acceptable dosages in man based e.g. on the examples set forth herein. In particular the formulas for dose estimation taking into account a normalization of body surface area are useful (where the dose is expressed in mg/m$^2$ as part of the conversion), but also the formulas for simple body weight scaling (where animal doses are expressed in mg/kg) are useful. The latter is used when testing in various animals provides for a similar "No Observed Adverse Effect Level" measured in mg drug per kg body weight. However, as the simple body weight scaling will provide for generally higher doses in man, the body surface normalization method is the safest. Table 3 in the FDA Guideline provides that e.g. mouse doses in mg/kg are converted to human doses in mg/kg according to the following formulas:

Human dose (mg/kg)=Murine dose (mg/kg)/12.3
normalization to body surface area method
Human dose (mg/kg)=Murine dose (mg/kg)×(weight of mouse/weight of human)
simple body weight scaling.

If one uses the dosages used in the examples (25 mg/kg and 50 mg/kg), the corresponding dose in a human of 60 kg body weight would be 2.0 and 4.1 mg/kg with the surface area normalization method, and 8.3 and 16.6 mg/kg using simple body weight scaling.

The administration may be continuous as can be the case if the proCTSD/proCTSB/proCTSL is delivered into the cerebrovascular fluid, or intermittent, such as such as at most or exactly 1, 2, 3, 4, 5, and 6 administrations per day. As is clear from the examples, the proCTSD/proCTSB/proCTSL exhibits a prolonged serum half-life meaning that administrations may be intermittent with intervals >1 day, e.g. weekly intervals. Most important is to ensure an effective concentration of the proCTSD/proCTSB/proCTSL in the patient. Persons skilled in pharmacology will readily be able to titrate an optimized dosage regimen for the patients, e.g. based on repeated measurements of proCTSD/proCTSB/proCTSL levels after administration.

In some preferred embodiments, the disease treated is NCL and selected from the group consisting of NCL type 1, type 2, type 3, type 4, type 5, type 6, type 7, type 8, type 9, type 10, type 11, types 12, type 13, and type 14, cf. above.

In other preferred embodiments, the disease treated is synucleinopathy, which is selected from Parkinson's disease, dementia with Lewy bodies (such as Alzheimer's disease), and multiple system atrophy.

In yet other preferred embodiments the disease treated is an autophagic flow block disease selected from the group consisting of Alzheimer's disease, Amyotrophic lateral sclerosis, Huntington's disease, Parkinson's disease, Danon disease and other lysosomal storage disorders where an block in autophagic flow is a common pathological hallmark (e.g. Pompe Disease and Niemann Pick Type C disease).

As shown in Example 9, intracranial administration of rhCTSD reduces the aggregation of insoluble α-synuclein in both an in vitro and an in vivo model. Since e.g. Parkinson's disease is a slowly progressing disease, treatments disclosed herein will be able to at least delay the progress of the disease if applied at a relatively early stage, because pathological aggregation of α-synuclein prevented/delayed. In some embodiments, the treatment would also involve direct reduction in already established aggregates of α-synuclein and e.g. be able to salvage cells that are otherwise lethally damaged by the aggregates.

An attractive approach could be to effect local production in the ependymium in Plexus choroideus by e.g. a introduction of a mechanical device or by introduction of genetically modified cells, which preferably would be confined to an environment that prevents migration into other tissue by the genetically modified cells.

In order to enhance the efficacy of the treatment or to broaden the scope of treatment, the proCTSD/proCTSD/proCTSL or their variants may be co-administered in any combination and/or with other enzymes such as pharmaceutically effective and acceptable amounts of proCathepsin F, i.e. any one of these pro-proteases and their variants disclosed herein may be administered in any possible combination. Administration of any one of the following combinations is thus within the scope of the invention:

proCTSD and proCTSB; proCTSD and proCTSL; proCTSD and proCTSF; proCTSB and
proCTSL; proCTSBD and proCTSF; proCTSL and proCTSF; proCTSD and proCTSB and
proCTSL; proCTSD and proCTSB and proCTSF; proCTSD and proCTSL and proCTSF;
proCTSB and proCTSL and proCTSF; and proCTSD and proCTSB and proCTSL and proCTSF.

Embodiments of the second and 3$^{rd}$ aspects of the invention

In the 2$^{nd}$ aspect, which relates to pro-cathepsin D (proCTSD), which comprises an amino acid sequence comprising at most 20 amino acid substitutions or deletions compared SEQ ID NO: 3, for use in a method of treatment of NCL or synucleinopathy or a condition/disease characterized by block of autophagic flow, all considerations relating to reagents and conditions discussed above in the context of the first aspect of the invention apply mutatis mutandis to this aspect. In other words, the treatment for which the proCTSD is used in the second aspect of the invention has the same characterizing features as discussed above for the method of the first aspect of the invention.

In the $3^{rd}$ aspect, which relates to pro-cathepsin B (proCTSB), which comprises an amino acid sequence comprising at most 20 amino acid substitutions or deletions compared SEQ ID NO: 9, for use in a method of treatment of NCL or synucleinopathy or a condition/disease characterized by block of autophagic flow, all considerations relating to reagents and conditions discussed above in the context of the first aspect of the invention apply mutatis mutandis to this aspect. In other words, the treatment for which the proCTSB is used in the third aspect of the invention has the same characterizing features as discussed above for the method of the first aspect of the invention.

In the $4^{th}$ aspect, which relates to pro-cathepsin D (proCTSD), which comprises an amino acid sequence comprising at most 20 amino acid substitutions or deletions compared SEQ ID NO: 3, for use in a method of treatment of NCL or synucleinopathy or a condition/disease characterized by block of autophagic flow, all considerations relating to reagents and conditions discussed above in the context of the first aspect of the invention apply mutatis mutandis to this aspect. In other words, the treatment for which the proCTSD is used in the second aspect of the invention has the same characterizing features as discussed above for the method of the first aspect of the invention.

Preparation of proCTSD/proCTSB/prCTSL

Typically, the proCTSD/proCTSB/proCTSL used in the invention will be prepared by recombinant gene technology. For the purposes of exemplification, the following general description uses the nucleic acid sequence SEQ ID NO: 1 as a starting point for such recombinant production, but any nucleic acid encoding proCTSD or proCTSB or proCTSL— e.g. a nucleic acid, the sequence of which has been codon optimized—is useful for the same purpose. In the examples is provided one specific preparation process, but as will be clear from the following, there are numerous ways to obtain a recombinant product. It should also be added that production of the proCTSD/proCTSB/proCTSL via solid phase or liquid phase polypeptide synthesis is also within the scope of the present invention. At any rate, any considerations provided in the following for recombinant production of proCTSD using SEQ ID NO: 1 as a starting point applies mutatis mutandis to recombinant production of proCTSB using SEQ ID NO: 7 as a starting point and for recombinant production of proCTSL from the wild-type nucleic acid sequence encoding SEQ ID NO: 13.

SEQ ID NO: 1 will be incorporated into a suitable expression vector according to methods known to the skilled person. Such vectors are discussed infra.

One vector for use to prepare the proCTSD invention comprises in operable linkage and in the 5'-3' direction, an expression control region comprising an enhancer/promoter for driving expression of the nucleic acid fragment encoding a polypeptide comprising SEQ ID NO: 3 (if SEQ ID NO: 1 is not used, a nucleic acid sequence that can include a signal peptide coding sequence may be used), a nucleotide encoding a polypeptide comprising SEQ ID NO: 3, and optionally a terminator. Hence, such a vector constitutes an expression vector useful for effecting production in cells of proCTSD. Since the polypeptides of the human of origin, recombinant production is conveniently effected in eukaryotic host cells, so here it is preferred that the expression control region drives expression in eukaryotic cell such as a bacterium, e.g. in E coli. However, if the vector is to drive expression in a prokaryotic cell, the expression control region should be adapted to this particular use.

The vector may be one that is capable of being integrated into the genome of a host cell—this is particularly useful if the vector is use in the production of stably transformed cells, where the progeny will also include the genetic information introduced via the vector. For transient expression, the ability to be integrated is of less value.

Typically, the vector is selected from the group consisting of a virus, a bacteriophage, a plasmid, a minichromosome, and a cosmid.

Viral vectors may be selected from the group consisting of a retrovirus vector, such as a lentivirus vector, an adenovirus vector, an adeno-associated virus vector, and a pox virus vector.

A more detailed discussion of vectors is provided in the following:

ProCTSD/proCTSB/proCTSL is typically encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques, see e.g. "Molecular Cloning, A Laboratory Handbook, $4^{th}$ edition by Green and Sambrook, ISBN-10: 1936113422. In addition to encoding the proCTSD/ proCTSB/proCTSL, a vector may encode polypeptide sequences such as a purification tag. Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Useful vectors for use to prepare proCTSD/proCTSB/ proCTSL may be used in a host cell to produce a proCTSD/ proCTSB/proCTSL that may subsequently be purified for administration to a subject.

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including polymerase chain reactions, in connection with the compositions disclosed herein (see U.S. Pat. Nos. 4,683,202, 5,928,906).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (cf. Molecular Cloning, A Laboratory Handbook, $4^{th}$ edition by Green and Sambrook, ISBN-10: 1936113422) The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to those that encode Immunoglobulin Heavy Chain, Immunoglobulin Light Chain, T Cell Receptor, HLA DQα and/or DQβ, β-Interferon, Interleukin-2, Interleukin-2 Receptor, MEW Class II 5, MHC Class II HLA-DRα, β-Actin, Muscle Creatine Kinase (MCK), Prealbumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), αl-Antitrypain, H2B (TH2B) Histone, Mouse and/or Type I Collagen, Glucose-Regulated Proteins (GRP94 and GRP78), Rat Growth Hormone, Human Serum Amyloid A, Troponin I, Platelet-Derived Growth Factor, Duchenne Muscular Dystrophy, SV40, Polyoma, Retroviruses, Papilloma Virus, Hepatitis B Virus, Human Immunodeficiency Virus, Cytomegalovirus, and Gibbon Ape Leukemia Virus.

Inducible Element systems include, but are not limited to MT II—Phorbol Ester (TFA)/Heavy metals; MMTV (mouse mammary tumor virus)—Glucocorticoids; β-Interferon-poly(rl)x/poly(rc); Adenovirus 5 E2—E1A; Collagenase—Phorbol Ester; Stromelysin—Phorbol Ester; SV40—Phorbol Ester; Murine MX Gene—Interferon, Newcastle Disease Virus; GRP78 Gene—A23187; α-2-Macroglobulin—IL-6; Vimentin—Serum; MEW Class I Gene H-2κb—Interferon; HSP70—E1A/SV40 Large T Antigen; Proliferin—Phorbol Ester/TPA; Tumor Necrosis Factor—PMA; and Thyroid Stimulating Hormone a Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of a protein encoding polynucleotide is not believed to be critical, so long as it is capable of expressing the polynucleotide in a targeted cell, preferably a eukaryotic cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a polynucleotide. The use of other viral or mammalian cellular or bacterial phage promoters, which are well known in the art, to achieve expression of polynucleotides is contemplated as well.

In embodiments the promoter is one that is not down-regulated by cytokines or one that is strong enough that even if down-regulated, it produces an effective amount of the protein/polypeptide. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

The use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819).

2. Multiple Cloning Sites

Vectors can include a multiple cloning site (MCS), which is a nucleic acid region that contains multiple restriction enzyme sites, any of which can be used in conjunction with standard recombinant technology to digest the vector. Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors encoding proCTSD/proCTSB/proCTSL, vectors containing genomic eukaryotic sequences may require donor and/or acceptor splicing sites to ensure proper processing of the transcript for protein expression. However, since SEQ ID NO: 1 and 7 and similar sequences are cDNA, the necessity for introduction of splicing sites is not of utmost importance.

4. Termination Signals

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail are more stable and are translated more efficiently. Thus, when using the preferred eukaryotic expression systems, it is preferred that that terminator comprises a signal for the cleavage of the RNA, and it is more preferred that the terminator signal promotes polyadenylation of the message.

Terminators contemplated for use in the preparation of proCTSD/proCTSB/proCTSL include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

Cells containing a nucleic acid construct encoding proCTSD/proCTSB/proCTSL may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

8. Transformed Cells

Transformed cells are useful as organisms for producing proCTSD/proCTSB/proCTSL, but also as simple "containers" of nucleic acids and vectors of the invention.

Certain transformed cells are capable of replicating the nucleic acid fragment encoding proCTSD/proCTSB/proCTSL. Preferred transformed cells of the invention are capable of expressing this nucleic acid fragment.

For recombinant production the transformed cell according may be prokaryotic, such as a bacterium, but also eukaryotic cells are useful.

Suitable prokaryotic cells are bacterial cells selected from the group consisting of *Escherichia* (such as *E. coli*), *Bacillus* (e.g. *Bacillus subtilis*), *Salmonella*, and *Mycobacterium* (*M. bovis* BCG).

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell is stably transformed by having the nucleic acid encoding proCTSD/proCTSB/proCTSL stably integrated into its genome, and in certain embodiments it is also preferred that the transformed cell secretes or carries on its surface the proCTSD/proCTSB/proCTSL, since this facilitates recovery. A particular version of this entails that the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly relevant.

Further Details on Cells and Cell Lines are Presented in the Following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Molecular Cloning, A Laboratory Handbook, 4$^{th}$ edition by Green and Sambrook, ISBN-10: 1936113422.

As used herein, the terms "cell", "cell line", and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JM1 09, and KCB, as well as a number of commercially available bacterial hosts such as SURE® Competent Cells and SOLOPACK™ Gold Cells (STRATAGENE®, La Jolla, CA). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Over the recent years, other types of host cells have emerged, e.g. plant cells used in plant cell based expression systems, and also insect cells such as *Drosophila* cells show promise.

9. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, and which can be bought, for example, under the name MAXBAC® 2.0 from INVITROGEN® and BAC-PACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Compositions Comprising proCTSD/proCTSB/proCTSL

Also within the Scope of this disclosure are compositions and dosage forms comprising proCTSD and/or proCTSB and/or proCTSL as described herein. The composition can be the media or supernatant containing the proCTSD/proCTSB/proCTSL that can be produced according to a method described herein.

The proCTSD/proCTSB/proCTSL described herein can be provided to a subject in need thereof alone or as such as an active ingredient, in a pharmaceutical formulation. As such, also described herein are pharmaceutical formulations containing an amount of a proCTSD/proCTSB/proCTSL. In some embodiments, the pharmaceutical formulations contain a therapeutically effective amount of a proCTSD/proCTSB/proCTSL. The pharmaceutical formulations described herein can be administered to a subject in need thereof as detailed above.

The pharmaceutical formulations containing a therapeutically effective amount of a proCTSD and/or proCTSB and/or proCTSL described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the therapeutically effective amount of a of a proCTSD and/or proCTSB and/or proCTSL described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-w, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbiturates, hydroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenydramine, carbinoxamine, cetirizine, chlorpromazine, cyclizine, chlorpheniramine, clemastine, cyproheptadine, desloratadine, dexbrompheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and $\beta_2$-adrenergic agonists.

Suitable anti-infectives include, but are not limited to, amebicides (e.g. nitazoxanide, paromomycin, metronidazole, tinidazole, chloroquine, miltefosine, amphotericin b, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethambutol, rifampin, rifabutin, rifapentine, capreomycin, and cycloserine), antivirals (e.g. amantadine, rimantadine, abacavir/lamivudine, emtricitabine/tenofovir, cobici stat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpivirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, asparginase *Erwinia chrysanthemi*, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid Formulation of proCTSD/proCTSB/proCTSL (Dosage Forms)

For the purposes of administering proCTSD and/or proCTSB and/or proCTSL, it/they is/are formulated in a manner suitable for the selected route of administration.

Dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravitreal, intracerebral, and intracerebroventricular and intradermal. Such formulations may be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 1 ng to 1000 g of a pharmaceutical formulation containing a therapeutically effective amount or an appropriate fraction thereof of proCTSD/proCTSB/proCTSL or composition containing the proCTSD/proCTSB/proCTSL. The oral dosage form can be administered to a subject in need thereof.

The dosage forms described herein can be microencapsulated. The dosage form can also be prepared to prolong or sustain the release of proCTSD and/or proCTSB and/or proCTSL. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds.

Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the proCTSD and/or proCTSB and/or proCTSL, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the proCTSD/proCTSB/proCTSL, the composition containing proCTSD/proCTSB/proCTSL, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the proCTSD/proCTSB/proCTSL, the composition containing a proCTSD/proCTSB/proCTSL, and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a proCTSD/proCTSB/proCTSL, composition containing proCTSD/proCTSB/proCTSL, or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation.

For some dosage forms suitable and/or adapted for inhaled administration, the pharmaceutical formulation is a dry powder inhalable formulation. In addition to the proCTSD/proCTSB/proCTSL, the composition containing a proCTSD/proCTSB/proCTSL, an auxiliary active ingredient, and/or pharmaceutically acceptable salt thereof, such a dosage form can contain a powder base such as lactose, glucose, trehalose, manitol, and/or starch. In some of these embodiments, the proCTSD/proCTSB/proCTSL, the composition containing proCTSD/proCTSB/proCTSL, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the proCTSD/proCTSB/proCTSL or compositions containing the proCTSD/proCTSB/proCTSL described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the proCTSD/proCTSB/proCTSL or composition containing a proCTSD/proCTSB/proCTSL per unit dose. In an embodiment, the predetermined amount of the proCTSD/proCTSB/proCTSL or composition containing a proCTSD is a therapeutically effective amount of the proCTSD or composition containing a proCTSD/proCTSB/proCTSL to treat or prevent a disease as disclosed herein. In other embodiments, the predetermined amount of the proCTSD/proCTSB/proCTSL or composition containing a proCTSD/proCTSB/proCTSL can be an appropriate fraction of the therapeutically effective amount of the active ingredient. Such unit doses may therefore be administered once or more than once a day. Such pharmaceutical formulations may be prepared by any of the methods well known in the art.

The invention will be illustrated by the following non-limiting examples:

Example 1

Preparation of Recombinant Human Pro-Cathepsin-D
Materials and Methods
Cloning of DNA
Human pro-Cathepsin-D cDNA flanked by NheI (5') and NotI (3') restriction sites was synthesized by Life Technologies GmbH (Darmstadt, Germany) based on the cDNA sequence AAA51922.1 (European Nucleotide Archive), SEQ ID NO: 1. Using the mentioned restriction sites the pro-CTSD cDNA was cloned into the pCEP-Pu vector (kindly provided by Prof. Joachim Grötzinger, University of Kiel), which includes upstream of the insert coding regions for the secretion signal peptide from secreted protein acidic and rich in cysteine (SPARC) and for a hexa-histidinyl tag. The pCEP-Pu vector also contains an EBV origin of replication (oriP) for episomal maintenance of the plasmid.

HEK EBNA Cells
Human embryonic kidney (HEK) 293 cells stably expressing the Epstein-Barr virus nuclear antigen 1 under the control of the CMV promoter (HEK 293-EBNA) were acquired from Invitrogen. Cells were maintained in Dulbecco's modified Eagle medium (DMEM; Life Technologies, 41965) containing 4 mM L-glutamine and 4.5 g/L glucose and supplemented with 10% (v:v) foetal bovine serum (Biochrom AG, S0115), 1% PenStrep (Sigma, P0781) and 0.25 mg/mL G-418 (Life Technologies, 11811-023) in a humidified 5% $CO_2$ atmosphere at 37° C.

Stable Cell Line Production
HEK 293-EBNA cells were transfected with pCEP-Pu containing pro-CTSD as follows: $2\times10^6$ were seeded in a 10 cm cell culture dish and transfected 24 h later using polyethylenimine (PEI) according to the manufacturer's instructions. 48 hours later, expressing cells were selected with 0.25 mg/ml G-418 and 1 µg/mL puromycin for 3 weeks. A high producing stable clone was selected by serial dilution followed by assessment of the levels of human recombinant pro-CTSD (rhproCTSD) secreted by the various clones.

rhproCTSD Production and Purification
Routinely, rhproCTSD was produced by seeding $4\times10^6$ cells in five 175 $cm^2$ cell culture flasks with 35 mL DMEM (supplemented with 10% FBS, 1% PenStrep, 0.25 mg/mL G-418, and 1 µg/mL puromycin). After the cells reached confluency the medium was replaced by 100 mL DMEM supplemented with 2.5% FBS and 1% PenStrep per flask. The medium was harvested after one week and the cell culture supernatant filtrated using a paper filter followed by vacuum filtration with Stericup (0.22 µm, Millipore, Germany). The sample was then concentrated to a final volume of 50 mL via an Amicon system and an ultrafiltration disk with a 10 kDa cutoff (Millipore, PLGC07610). Recombinant protein was purified via its N-terminal His-tag using a His-Trap 1 mL column (GE Healthcare, Munich) on an Aekta Purifier (GE Healthcare) and eluted with 250 mM imidazole in phosphate buffered saline pH 7.4 (PBS: 137 mM NaCl, 2.7 mM KCl, 10 mM $Na_2HPO_4$, 1.8 mM $KH_2PO_4$). The protein was further purified via size exclusion chromatography on a Superdex 75 column (GE Healthcare). Finally rhproCTSD was concentrated using a Vivaspin 20 tube with 10 kDa cutoff (Sartorious, VS2002).

Example 2

Uptake and Processing of rhproCTSD by CTSD-Deficient Mouse Embryonic Fibroblasts
Materials and Methods
Mouse Embryonic Fibroblast (MEF) Isolation
To isolate mouse embryonic fibroblasts (MEFs) $CTSD^{+/-}$ mice were mated. Pregnant female $CTSD^{+/-}$ mice were sacrificed at day 13.5 post coitum. Both uterine horns were prepared and placed in a Petri dish containing sterile PBS. Each embryo was separated from its placenta and amniotic sac and transferred to a fresh Petri dish with PBS. Embryo heads were removed and used for genotype determination using the DirectPCR® Lysis Reagent Tail (Peqlab) and proteinase K digestion. Furthermore, all red organs were dissected. In a 3.5 cm culture dish containing 2 mL of trypsin/EDTA (0.5 mg/mL/0.22 mg/mL in PBS) the remaining tissue was minced using a razor blade and incubated for 15 minutes at 37° C. Single cells were collected in culture medium and the suspension spun down at 300×g and room temperature for 5 minutes. The pellets containing the fibroblasts were resuspended in 10 mL culture medium and added to one 10 cm culture dish per embryo. MEFs were immortalized by transfection of the SV40 large T antigen.

Uptake Experiments
Approximately $1\times10^6$ $CTSD^{+/+}$ or $CTSD^{-/-}$ MEF cells were seeded per well of 6 well plates. The cells were allowed to attach overnight. Starting the following day 20 µg/mL rhproCTSD in PBS was added to the media of $CTSD^{-/-}$ MEFs at different time points (48, 40, 24, 16, 8, 6, 4, 2, 1 and 0.5 h). The cellular uptake of rhproCTSD was then evaluated by immunoblot and CTSD activity assay. To test the processing and uptake route the following inhibitors were co-incubated with rhproCTSD: leupeptin (25 µM, Enzo Life Sciences, ALX-260-009-M025), mannose-6-phosphate (10 mM, Sigma, M6876-10MG), mannose (Serva, 28460) and receptor-associated protein (RAP, 750 nM, kindly provided by Prof. Thomas Braulke).

Western Blot
The cells were then washed thrice with PBS and lysed in 150 µL RIPA buffer (150 mM NaCl, 50 mM Tris-HCl, pH 7.4, 2 mM EDTA, 10 mM NaF, 1 mM $Na_3VO_4$, 1 mM PMSF [Sigma, P7626]) 0.5% sodiumdeoxycholate, 1% Triton X-100 [Sigma, X100], supplemented with 1× cOmplete Protease Inhibitor Cocktail [Roche])

by shaking for 1 h at 4° C. Lysates were cleared by centrifugation at 4° C. for 15 min at 12,000×g and protein concentrations were determined using the BCA method (Thermo Fisher Scientific, 23225). The samples were denatured with 5× Laemmli buffer (50% (v/v) 1 M Tris-HCl, pH 6.8, 50% (v/v) 100% glycerol, 10% (w/v) DTT, 10% (w/v) SDS, 0.01% (w/v) bromophenol blue), boiled for 4 min at 100° C. and separated by electrophoresis on 12.5% (w/v) SDS-PAGE gel running continuously at 90 V. Proteins were transferred to a nitrocellulose membrane using the semi-dry Western blot method (65 mA per gel for 2 h). The membranes were blocked with 5% milk in TBS-T (20 mM Tris/HCl pH 7.0, 150 mM NaCl, 0.1% (v/v) Tween® 20).

CTSD Activity Assay

Cells were lysed for 30 min at 4° C. with shaking in 150 µL of 50 mM sodium acetate (pH 5.5), 0.1 M NaCl, 1 mM EDTA, and 0.2% Triton X-100. Lysates were clarified by centrifugation and immediately used for determination of proteolytic activity. For this, 2 µL of cell lysates were incubated at 37° C. for 60 min in lysis buffer (100 µL) with 10 of CTSD and E substrate (Enzo Life Sciences, P-145). The AMC released as a result of proteolytic activity was quantified with a microtiter plate reader (exc: 360 nm; em: 440 nm, band pass 40), and normalized to total protein content.

Immunohistochemistry

Approximately $0.5\times10^6$ CTSD$^{+/+}$ or CTSD$^{-/-}$ MEF cells were seeded per well of a 6 well plate (with 13 mm coverslips). The cells were allowed to attach overnight. The following day 20 µg/mL rhproCTSD in PBS was added to the media of CTSD$^{-/-}$ MEFs. After 24 h, the cells were washed thrice with PBS fixed with 99% cold methanol for 20 min at room temperature. After permeabilization and blocking (PBS with 10% FBS and 0.2% saponin) coverslips were incubated overnight with rabbit anti-CTSD (kindly provided by Prof. Andrej Hasilik) and rat anti-LAMP1 (1D4B, DSHB) antibodies diluted 1/500 in blocking buffer. After incubation with fluorophoreconjugated secondary antibodies (Alexa Fluor; Thermo Fisher Scientific) and washing, coverslips were embedded in mounting solution. Images were analyzed with an Olympus FV1000D Laser Scanning Confocal Microscope (model: FV10-292-115) with a 1003 lens (UPLSAPO 1003 numerical aperture [NA]: 1.40). Image acquisition was performed with the FV10-ASW 4.2 Viewer software (Olympus, Germany).

Results

It was examined whether rhproCTSD can be taken up and processed by mouse embryonic fibroblasts (MEFs) deficient in CTSD. Exposure of MEFs to 40 µg of rhproCTSD (20 µg/mL medium) in the culture media resulted in a gradual uptake of rhproCTSD. After exposure for 30 minutes only the full length pro-CTSD could be observed intracellularly. However, after four hours clear bands corresponding to the 48 kDa single chain intermediate and to the 34 kDa heavy chain of mature CTSD (mCTSD) could be observed. This proteolytic processing reflects the transport of the protein to the lysosomes, where the final cleavage mediated by cysteine cathepsin-B and -L takes place. In agreement, inhibition of cysteine cathepsins with leupeptin resulted in decreased CTSD processing and reduced mCTSD levels. The levels of mCTSD continued to increase until reaching a plateau after 24 hours of incubation. This indicates that rhproCTSD is being taken up by the murine cells and regularly processed to mCTSD. Immunohistochemistry analysis corroborated the delivery of rhproCTSD to LAMP1-positive endolysosomes. CTSD activity levels as assessed by a fluorometric assay increased in parallel to the levels of mCTSD protein, significantly increasing after 4 h and plateauing after 24 h. This suggests that the mCTSD formed in lysosomes through the processing of rhproCTSD is active.

To clarify the nature of the receptor mediating the endocytosis of rhproCTSD into MEF cells a competition experiment was carried out with free mannose-6-phosphate (M6P), mannose and the LRP1 antagonist receptor-associated protein (RAP). Co-incubation of 40 µg rhproCTSD with (10 mM) M6P and (750 nM) RAP but not with (50 mM) mannose prevented the delivery of rhproCTSD to the lysosomal compartment, as evidenced by the reduced levels of mCTSD protein and activity. In general, this demonstrates that the delivery of rhproCTSD to the endolysosomal compartment is mediated by M6P and LRP-1 receptors.

Example 3

Uptake of rhproCTSD by In Vitro NCL Models

Materials and Methods

CLN3 Knock-in Mouse Immortalized Cerebellar Cells

CbCln3$^{\Delta ex7/8}$ neuronal precursor cell lines, kindly provided by Susan L. Cotman (MTA with Massachusetts General Hospital, Boston, MA, USA), were established by conditionally immortalizing cerebellar granule neurons from postnatal wild-type, heterozygous or homozygous littermate Cln3$^{\Delta ex7/8}$ mice. These mice carry a ~1 kb genomic deletion in the endogenous murine Cln3 gene that is analogous to the most common ~1 kb genomic deletion in juvenile NCL patients. Cells were maintained in in "Cbc" media (DMEM [Life Technologies, 41965], 10% heat-inactivated fetal bovine serum [Biochrom AG, 50115], 24 mM KCl, 1% PenStrep [Sigma, P0781], lx Glutamax [Gibco™ 35050061] and G418 [200 µg/ml]), in a humidified incubator maintained at 33° C., 5% $CO_2$ atmosphere.

Isolation of Primary Mouse Cortical Neurons

Primary cortical neuron cultures were prepared from embryons (E16) as previously described in Labonté D et al. (2014), *Eur J Cell Biol* 93: 338-346. Briefly, 6 well plates were coated with poly-L-lysine (100 µg/ml in PBS, Sigma, P2636). 250,000 cells were then seeded in Lonza PNGM medium (CC-4461). Following one week of recovery 20 µg/mL rhproCTSD was added to the culture medium. After one week the cells were processed as described above in Example 2 under the "Western blot" heading.

Preparation of Murine Organotropic Hippocampal Slices

Organotypic hippocampal slice cultures were prepared from P5 CTSD$^{-/-}$ and CTSD$^{+/+}$ littermates as previously described in Mikhaylova M et al. (2018), Neuron 97: 1110-1125.e14. Briefly, mice were decapitated, brains removed, placed in preparation medium (HAME-01 Prep Medium, Cell Concepts, Umkirch, Germany) and hippocampi dissected under a binocular. Perpendicular slices of 350-400 µm thickness were cut using a McIlwain tissue chopper (Mickle Laboratory Engineering, Surrey, UK). After separating the slices in fresh preparation medium, only excellent quality slices were transferred onto millicell membranes (3 slices per membrane, Merck Millipore) placed in 6 well-plates with pre-warmed and $CO_2$ equilibrated 1 mL OHSC medium. Slices were cultured at 37° C., 5% $CO_2$, humidity. Feeding of slices was performed by exchanging 0.9 ml of medium at DIV2 and thereafter every 3 days. After 5 days recovery 10 µg/mL rhproCTSD in PBS was added to the culture media. The slices were exposed to rhproCTSD for 5 days.

Human CLN10 Patient Fibroblasts

Human fibroblast cultures derived from skin biopsies of confirmed CLN10 patients being followed at the University Medical Center Hamburg-Eppendorf were kindly provided by Dr. Angela Schulz. The cells were cultured in DMEM medium (Life Technologies, 41965) supplemented with 10% (v:v) fetal bovine serum (Biochrom AG, 50115) and 1% PenStrep (Sigma, P0781) in a humidified 5% $CO_2$ atmosphere at 37° C.

Results

The uptake of rhproCTSD was tested in control and CLN10 patient fibroblasts as well as in CTSD-deficient primary cortical and hippocampal neurons. In all cell lines tested rhproCTSD was taken up and processed to the mature lysosomal form.

A correction of autophagic flow was also observed as revealed by a reduction of the autophagy-associated proteins LC3-II and p62 in cultured primary mouse cortical neurons as well as in hippocampal brain slices. Using murine cerebellar cell lines derived from another CLN3 knock-in mouse model it was shown that the application of rhproCTSD improved the cellular pathology observed suggesting that the presently disclosed therapeutic approach may also be effective in other types of NCL.

Example 4

Uptake of rhproCTSD by CLN10 Mice

BACKGROUND

CTSD-deficient mice were generated by using the targeting construct pCDneo4 to disrupt of the Ctsd gene in embryonic stem cells (as described in Saftig Petal. (1995), EMBO J 14: 3599-3608. The open reading frame (ORF) of the gene was interrupted in exon 4 leading to a null mutation. CTSD-deficient mice constitute a good phenocopy of CLN10, displaying the most dramatic NCL phenotype. Mice without CTSD develop normally until 14 days of postnatal life, after which the animals start losing weight early on and develop seizures, progressive retinal atrophy, gait and neurological abnormalities resulting in death around postnatal day 25. Pathologically the mice are characterized by lysosomal storage of autofluorescent ceroid lipofuscin, neuroinflammation and accumulation of autophagic vacuoles in neuronal and visceral tissues.

Materials and Methods

CTSD-Deficient (CLN10) Mice $CTSD^{-/-}$ mice were bred from heterozygous founders and genotyped as previously described (Saftig P et al. (1995), EMBO J 14: 3599-3608). All animals were housed in individually ventilated cages (IVC) to generate a specific pathogen-free environment. The room temperature was maintained at 19-22° C. with a humidity of 45-60% and light conditions of 12 h lighting followed by 12 h darkness were applied in turns. Access to water and standard laboratory animal food (pellets by Ssniff Spezialdiaten) was granted ad libitum. Animal handling and care were performed in agreement with the German animal welfare law according to the guidelines of the Christian Albrechts University of Kiel. Experiments involving animals were approved by the Ministry of Energy, Agriculture, the Environment and Rural Areas Schleswig-Holstein under the reference number V242-40536/2016(81-6/16).

Intravenous Injection of rhproCTSD $CTSD^{-/-}$ mice at post-natal day 19 (P19) were injected intravenously with 25 mg/Kg rhproCTSD in PBS (10 mL/Kg from a 2.5 mg/mL solution) via the tail vein using an insulin syringe (Gauge 30, BD MicroFine™)

Tissue Collection and Processing

Mice were sacrificed 2, 4, 8, 24 or 48 h after the injection. The animals were firstly anaesthetized by intra-peritoneal injection of 10 mg/mL Ketamine and 6 mg/mL Rompun® in 0.9% (w/v) NaCl solution and then transcardially perfused with phosphate buffer (PB) 0.1 M pH 6.8. Blood was collected directly from the right atrium of the heart prior to perfusion. Plasma was isolated by incubating the blood for 0.5 h at RT, followed by 1 hr at 4° C. and finally centrifugation for 30 min at 4500 rpm to clear red blood cells and platelets. The supernatant (plasma) was collected and frozen at −80° C. All tissues harvested were divided in two parts. One part was snap frozen in liquid N2 and stored at −80° C. for biochemistry and the other part was fixated in 4% (w/v) PFA in PB at RT for 4 h for immunohistochemical analysis. The fixed tissues were subsequently washed in PB at 4° C. overnight and then immersed in 30% sucrose in PBS and stored at 4° C. Semi-thin sections (35 μm) were cut on a Leica SM 2000 R sliding microtome (Leica Microsystems) with dry-ice cooling and stored in PBS containing 0.02% (w/v) sodium azide.

Biochemical Analysis

Samples were stored at −80° C. until homogenization in 1:10 ratio of tissue-weight to volume of PBS with 0.1% (v/v) Triton X-100 and protease inhibitor cocktail. The tissues were homogenized with three porcelain beads (PeqLab, 91-PCS-CK14B) in 2 mL screw-cap Eppendorf tubes, samples were crushed with a Precellys® 24 homogenizer (Bertin) set at 6 m $s^{-1}$ for 20 s, twice, with samples kept on ice in between runs. Lysates were isolated from glass beads by pipetting into sterile 1.5 mL Eppendorf tubes. Protein concentration of the homogenates was determined as described above in Example 2 (under the description of Western blot) and used for Western blot and CTSD activity assay as described in Example 3.

Immunohistochemistry

After blocking unspecific antibody binding sites of the slices with blocking solution (0.5% Triton X-100, 4% normal goat serum in PB), the sections were incubated with the primary antibodies overnight at 4° C. in blocking solution. After three washing steps in washing buffer (0.25% Triton X-100 in PB) sections were incubated with AlexaFluor 488-conjugated secondary antibodies for 2 hours at room temperature (and AlexaFluor 647 for double-labelling), washed again 3 times in washing buffer, and finally coverslipped in Mowiol/DABCO. An Olympus FV1000 confocal laser scanning microscope was used for image acquisition (see section 4.1.3.)

Results

Preliminary in vitro studies indicate that the purified rhproCTSD is rather stable when stored in PBS at 4° C. (no signs of breakdown up to 48 h) and even at 37° C. (only minor degradation after 48 h). The uptake and processing of rhproCTSD in CTSD-deficient mice was studied. For that the animals received 25 mg/Kg of rhproCTSD by intravenous injection (i.v.) in the tail vein and the fate of rhproCTSD was followed at different time points. The recombinant protease appears to be quickly taken up from the circulation, since 8 hours after the rhproCTSD injection only minor amounts of the enzyme could be detected in plasma by western blot. A rough estimation would suggest a half-life of approximately 4 hours for rhproCTSD in circulation. In the liver, 2 hours after injection high levels of proCTSD and mature CTSD (mCTSD) could be observed by immunoblot analysis. ProCTSD levels quickly decreased and after 4 hours almost only mCTSD was present in liver lysates. This suggests that liver cells quickly take up and process rhproCTSD to the active mCTSD final form. Accordingly, CTSD activity in the liver of CTSD$^{-/-}$ mice injected with recombinant enzyme increased steadily until 8 h post injection and then started to gradually decrease. These data suggest that the half-life of mCTSD in liver cells exceeds the 48 h. In conclusion, rhproCTSD is quickly taken up from the circulation and processed to the mature active form by hepatic cells.

Example 5

ERT with rhproCTSD in CLN10 Mice

BACKGROUND

The dose of rhproCTSD to be tested in CTSD$^{-/-}$ mice was chosen based on previous experience with ERT in other lysosomal storage diseases (Blanz J et al (2008), Hum Mol Genet 17: 3437-3445). The human equivalent dose (HED) to be used in future clinical studies will be calculated based on the ongoing pre-clinical studies in the CLN10 murine model using the principles set forth above in the general discussion of dosages.

Materials and Methods

Repeated dosing of rhproCTSD in CLN10 mice Mice were genotyped at post-natal day P3. Starting between P3-5 mice received one intraperitoneal (i.p.) injection of 50 mg/kg rhproCTSD (in PBS). After that, animals received four i.p. injections of 25 mg/kg (two per week) and one final intravenous injection of 25 mg/kg between P20-P21. At P23 mice were anaesthetized by intra-peritoneal injection of 10 mg/ml Ketamine and 6 mg/ml Rompun® in 0.9% (w/v) NaCl solution and transcardially perfused with phosphate buffer 0.1M. Tissue collection, biochemical and immuno-histochemical analysis was performed according to the procedures in Example 4.

Results

After repeated dosing of rhproCTSD, mature active CTSD (mCTSD) could be detected in all the tissues analyzed—liver, spleen, kidney, intestine, thymus, skeletal muscle and brain (minor levels). In the liver and spleen, CTSD activity was completely restored and lead to a correction of various pathological markers analyzed. Namely, the levels of the LAMP1 protein, a marker for late-endosomes and lysosomes, elevated in the liver of CTSD$^{-/-}$ untreated animals were completely normalized in CTSD$^{-/-}$-treated mice (see FIG. 1A). This indicates that the pathological hypertrophy of the lysosomal compartment caused by CTSD-deficiency is fully corrected. The enlargement of endo-lysosomes in the liver of untreated CTSD$^{-/-}$ is also blatant upon microscopic analysis, showing the presence of enlarged vacuolar structures. This vacuolization was fully reversed by the treatment with the protease (FIG. 1B). Another established pathological hallmark of NCL is the lysosomal accumulation of small hydrophobic proteins called saposins. Treatment with rhproCTSD lead to a significant reduction in the build-up of saposin C (SapC) and saposin D (SapD) in the liver, spleen and skeletal muscle of untreated age-matched controls (FIG. 1A and Table 2). A correction of autophagic flow was also observed as revealed by a reduction of the autophagy-associated protein LC3-II in the spleen of rhproCTSD-treated CTSD$^{-/-}$ mice when compared to untreated controls (FIG. 1C).

Table 2
Correction of markers of protein accumulation in peripheral tissues. Saposin C and Saposin D accumulation in liver, spleen and skeletal muscle of P23 CTSD$^{-/-}$ mice treated with rhproCTSD compared to age-matched PBS-injected CTSD$^{+/+}$ and CTSD$^{-/-}$ controls. Clearance of protein accumulation was considered to complete (+++) when the levels in CTSD$^{-/-}$-treated animals were identical to wild-type levels. Correction was considered nearly complete (++) when levels where only slightly higher than in wild-type controls.

|  | Saposin C | Saposin D |
| --- | --- | --- |
| Liver | +++ | ++ |
| Spleen | ++ | +++ |
| Skeletal muscle | ++ | ++ |

Example 6

Targeting the Central Nervous System with rhproCTSD

Background

Due to the limited amount of rhproCTSD that reaches the central nervous system (CNS) with the therapeutic strategy described above various approaches are being currently investigated to increase the amount of protease provided to the CNS. One of these approaches was devised by the Mayo Clinic (Rochester, Minnesota, USA) and employs a peptide—K16ApoE—composed of 16 lysines, which is a part of the ApoE protein that binds to the low-density lipoprotein receptor (LDLR) (see Sarkar G et al., PLoS One 9: e97655 and Meng Y et al. (2014), Mol Ther 22: 547-553). This peptide can be mixed directly with the therapeutic enzyme and thereby co-injected (i.v.) into the circulation of the animals, causing a temporary opening of the blood-brain barrier that allows the recombinant enzyme to uniformly reach the various regions of the brain (see Meng Y et al. (2014), Mol Ther 22: 547-553 and Meng Y et al. (2017), Mol Ther 25: 1531-1543. The mode of action of this peptide is not fully elucidated yet, but evidence suggests that it stimulates transcytosis creating transient channels that allow the passage of circulatory proteins. The dose of K16ApoE used in the preliminary studies (40 nmol per mouse) reported in the following was chosen based on the previously published studies mentioned above.

A second approach being explored is the delivery of therapeutic rhproCTSD directly to the CNS by intracerebroventricular injection (I.C.V.), a commonly used and well established method to directly deliver products to the cerebral lateral ventricles as described in e.g. Krasemann S et al., (2013), J Gen Virol 94: 453-463 and Altmeppen H C et al (2015), Elife 4: e04260.

Materials and Methods

Co-Injection of rhproCTSD and K16ApoE

The K16ApoE peptide was synthesized by LifeTein, LLC (South Plainfield, New Jersey, US) with a purity of 93%. The peptide was mixed with the rhproCTSD solution in PBS, briefly vortexed and incubated for 1 h at RT. A dose of 86 mg/Kg rhproCTSD with 40 nmol of K16ApoE was intravenously injected (injection volume of 10 ml/Kg) in a P20 CTSD$^{-/-}$ mouse via the tail vein. CTSD$^{+/+}$ and CTSD$^{-/-}$ littermate controls were i.v. injected with the same volume of PBS. After 24 h the mice were sacrificed and the brain distribution of rhproCTSD analyzed as described above in Example 4.

Results

Twenty-four hours after co-injection of rhproCTSD and K16ApoE a broad distribution of CTSD throughout the brain could be observed by immunohistochemistry, even reaching the deeper regions such as the thalamus. In all regions analyzed CTSD could be found in LAMP1-positive endo-lysosomes, indicating correct routing of the protease to lysosomes in brain cells. Immunoblot analysis of total brain lysates evidenced a complete restoration of mature CTSD protein to wild-type levels (FIG. 2). The levels of CTSD activity were also significantly increased in the brain of the injected animal.

Example 7

Effect of rhproCTSD on α-Synuclein Clearance

Materials and Methods

H4 cells are α-synuclein overexpressing human neuroglioma cells. Inducible α-synuclein expression is under the control of a tetracycline-inducible promoter (tet-off system). This means, upon addition of doxycycline, levels of overexpressed α-synuclein decrease (first description of the cell line in: Mazzulli et al. (2011) Cell: 146, 37-52). The H4 cell model is a widely used cell model for α-synuclein aggregation studies. For enzyme uptake studies, the rhproCTSD was added to the media (20 µg/ml) and incubated for different time points (24-72 hours). Then the cells were washed with PBS and lysed in Triton buffer (1%). For sequential extraction of soluble (triton soluble) and insoluble (SDS soluble) fractions, lysates were ultracentrifuged (55,000×g, 4° C., 30 min.) and the pellet was dissolved in SDS buffer (2%) and boiled. The samples were analysed by Western blot (see example 2 for Western Blot details) with PVDF membrane and PFA post-fixation (0.4%). Rabbit anti-α-synuclein C20 (Santa Cruz; 1:1000 in TB ST/Odyssey blocking buffer) was used for detection of ~17 kDa-sized α-synuclein.

Results

H4 cells overexpressing α-synuclein were treated with rhproCTSD as described in the material and method section above. A clearance of Triton-soluble α-synuclein was observed already after 24 h and of insoluble (SDS-soluble) after 72 h (see FIGS. 3A and 3B, respectively). Addition of doxycycline to the media leads to a decrease in α-synuclein expression and protein levels. The rate of α-synuclein clearance in the presence of doxycycline was accelerated in the presence of rhproCTSD. Also, in murine primary cortical neurons incubated for 7 days (see example 3 for incubation details) with rhproCTSD a partial clearance of soluble α-synuclein protein levels was observed.

Example 8

Preliminary Results with Pro-Cathepsin B

In analogy with the above methods disclosed for CTSD, recombinant human, His-tagged CTSB (rhproCTSB) has been produced in HEK EBNA cells and purified by a combination of affinity chromatography applied to the HEK EBNA culture medium, subsequence size exclusion chromatography, and final pooling and concentration.

In brief, human pro-Cathepsin-B cDNA flanked by NheI (5') and NotI (3') restriction sites was synthesized based on SEQ ID NO: 7. Using these restriction sites the pro-CTSB cDNA was cloned into the pCEP-Pu vector and transfected into HEK EBNA cells in the same manner as for proCTSD in example 1 and the subsequent purification and concentration followed the same procedure as described for proCTSD.

Further, uptake and processing of the purified rhproCTSB by CTSB deficient mouse embryonic fibroblasts (MEF) and CLN3 knock-in mouse immortalized cerebellar cells were tested in a manner analogous to Examples 2 and 3 for CTSD. The results confirm that the purified rhCTSB is processed to its active forms (primarily by cysteine proteases) within 18 hours in both MEF and HEK cells and that the enzyme is taken up by CLN3 cells. It was also established that the enzyme reaches the lysosomal compartment in the tested cells.

Finally, a pilot experiment in heterozygous and wildtype mice has confirmed the purified rhCTSB is taken up from the bloodstream within 6 hours after injection and that the enzyme thereafter exhibits a half-life of several days in the liver.

To conclude, the preliminary experiments have verified that also proCTSB can be recombinantly produced and that it after administration is activated intracellularly, that it reaches the relevant intracellular compartment (lysosomes) and that it exhibits a prolonged half-life after being administered to an animal model. Since the function of CTSB to a large extent is analogous to that of CTSD, it is therefore equally relevant to base a therapeutic approach on administration or co-administration with CTSD of CTSB.

Example 9

Pro-Cathepsin D in Models of Parkinson's Disease

In Parkinson's disease, intracellular accumulation of α-synuclein is lethal to domanergic neurons and in turn causes motor deficits. It is further known that lysosomal cathepsins degrade α-synuclein and that certain allelic variants of both CTSD and CTSB constitute genetic risk factors for Parkinson's disease.

In order to investigate the present inventive approach, treatment was made with rhCTSD of dopaminergic neurons:

An significant overall decrease of α-synuclein fluorescence intensity in rhCTSD treated dopaminergic neurons derived from Parkinson's disease patients was observed in immunofluorescence microscopy when comparing to dopaminergic neurons treated with phosphate buffered saline.

In parallel experiments, dopaminergic neurons derived from Parkinson's disease patients were treated with phosphate buffered saline, rhCTSD, and rhCTSB, respectively and subsequently the ratios α-synuclein/GAPDH and α-synuclein/βiii-tubulin were determined from SDS PAGE Western blots. The results obtained showed that rhCTSB seems to decrease soluble forms of α-synuclein more efficiently than rhCTSD, whereas but rhCTSD seems to more efficiently decrease insoluble (pathological) forms of α-synuclein.

In vivo experiments were also carried out in the CLN10 mouse model, where the CTSD gene has been knocked out. Mouse brain lysates were investigated in dot blot analyses:

First of all, it was observed that the pathological (insoluble) α-synuclein level (measured as intensity in the dot blots) was increased in the CTSD knock-out model CLN10 compared to wild-type mice whereas the benign form (insoluble) of α-synunclein was decreased. It was further observed that intracranial injections of rhCTSD in the CTSD knock-out mice essentially restored the wild-type phenotype with respect to the balance between soluble and insoluble α-synuclein. See FIG. 4, which shows the insoluble α-synuclein levels.

The invention claimed is:

1. A method of therapeutic and/or prophylactic treatment of a human being for a Neuronal Ceroid Lipofuscinosis (NCL) or synucleinopathy or disease characterized by block of autophagic flow comprising administration to the human being a pharmaceutically effective and acceptable amount of a pro-cathepsin selected from the group consisting of pro-cathepsin D (proCTSD), pro-cathepsin B (proCTSB), and pro-cathepsin L (proCTSL), or any combination thereof,
   wherein said proCTSD comprises an amino acid sequence comprising a total of at most 20 amino acid substitutions and amino acid deletions compared SEQ ID NO: 3, and
   wherein said proCTSB comprises an amino acid sequence comprising a total of at most 20 amino acid substitutions and amino acid deletions compared to SEQ ID NO: 9, and
   wherein said proCTSL comprises an amino acid sequence comprising a total of at most 20 amino acid substitutions and amino acid deletions compared to SEQ ID NO: 14, and
      wherein said proCTSD or proCTSB or proCTSL is co-administered or formulated with an agent that facilitates passage of the proCTSD/proCTSB/proCTSL across the blood-brain barrier, or
      wherein the proCTSD/proCTSB/proCTSL is coupled to a moiety, which facilitates passage of the proCTSD/proCTSB/proCTSL across the blood-brain barrier.

2. The method according to claim 1, wherein the pro-cathepsin does not include a signal peptide.

3. The method according to claim 1, wherein the proCTSD and/or proCTSB and/or proCTSLinclude(s) a purification tag.

4. The method according to claim 1, wherein the proCTSD consists of the amino acid sequence set forth in SEQ ID NO: 3, or a variant thereof comprising at most 20 amino acid substitutions or deletions and/or wherein the proCTSB consists of the amino acid sequence set forth in SEQ ID NO: 9, or a variant thereof comprising at most 20 amino acid substitutions or deletions and/or
   wherein the proCTSL consists of the amino acid sequence set forth in SEQ ID NO: 14, or a variant thereof comprising at most 20 amino acid substitutions or deletions.

5. The method according to claim 1, wherein the proCTSD upon entry into lysosomes can be activated into intermediate cathepsin D (iCTSD) and/or into mature cathepsin D (mCTSD),
   wherein the proCTSB upon entry into lysosomes can be activated into mature single chain cathepsin B (scmCTSB) and/or into two chain mature cathepsin B (tcmCTSB), and
   wherein the proCTSL upon entry into lysosomes can be activated into intermediate cathepsin L (iCTSL) and/or into mature cathepsin L (mCTSL).

6. The method according to claim 1, wherein the proCTSD and/or proCTSB and/or proCTSL is administered via the intraveneous or intraarterial or intravitreal route.

7. The method according to claim 1, wherein the maximum dosage in 24 hours is in the range between 0.1 and 1000 mg proCTSD per kg body weight and/or between 0.1 and 1000 mg proCTSB per kg body weight and/or between 0.1 and 1000 mg proCTSL per kg body weight.

8. The method according to claim 1, wherein administration of proCTSD and/or proCTSB and/or proCTSL is continuous.

9. The method according to claim 1, wherein administration of proCTSD and/or proCTSB and/or proCTSL is in the form of repeated administrations.

10. The method according to claim 1, wherein the NCL is treated and the NCL is selected from the group consisting of NCL type 1, type 2, type 3, type 4, type 5, type 6, type 7, type 8, type 9, type 10, type 11, types 12, type 13, and type 14.

11. The method according to claim 1, wherein synucleinopathy is treated and the synucleinopathy is selected from Parkinson's disease, dementia with Lewy bodies, and multiple system atrophy.

12. The method according to claim 11, wherein the dementia with Lewy bodies is Alzheimer's disease.

13. The method according to claim 1, wherein an autophagic flow block disease is treated, and where it is selected from the group consisting of Alzheimer's disease, Amyotrophic lateral sclerosis, Huntington's disease, Parkinson's disease, and Danon disease.

14. The method according to claim 1, which comprises co-administration of a pharmaceutically effective and acceptable amount of (pro)Cathepsin F.

15. The method according to claim 2, wherein the procathepsin does not include amino acid residues 1-20 of SEQ ID NO: 2, amino acid residues 1-17 of SEQ ID NO: 9, and amino acids 1-17 of SEQ ID NO: 14.

16. The method according to claim 3, wherein the purification tag is a His tag.

17. The method according to claim 5, wherein the proCTSD upon entry into lysosomes can be activated into intermediate cathepsin D (iCTSD) consisting of SEQ ID NO: 4 and/or into mature cathepsin D (mCTSD) consisting of a heterodimer of SEQ ID NO: 5 and SEQ ID NO: 6, wherein the proCTSB upon entry into lysosomes can be activated into mature single chain cathepsin B (scmCTSB) consisting of SEQ ID NO: 10 and/or into two chain mature cathepsin B (tcmCTSB) consisting of a heterodimer of SEQ ID NO: 11 and SEQ ID NO: 12, and wherein the proCTSL upon entry into lysosomes can be activated into intermediate cathepsin L (iCTSL) consisting of SEQ ID NO: 15 and/or into mature cathepsin L (mCTSL) consisting of a heterodimer of SEQ ID NO: 16 and SEQ ID NO: 17.

18. The method according to claim 9, wherein administration of proCTSD and/or proCTSB and/or proCTSL is in the form of 1, 2, 3, 4, 5, or 6 repeated administrations per day.

* * * * *